US009556452B2

(12) United States Patent
Wintermantel et al.

(10) Patent No.: US 9,556,452 B2
(45) Date of Patent: Jan. 31, 2017

(54) VACCINE FOR CONTROL OF BEET CURLY TOP VIRUS INFECTION OF PLANTS

(71) Applicant: The United States of America, as represented by the Secretary of Agriculture, Washington, DC (US)

(72) Inventors: William M Wintermantel, Salinas, CA (US); Laura L Hladky, Salinas, CA (US)

(73) Assignee: The United States of America, as Represented by the Secretary of Agriculture, Washington, DC (US)

( * ) Notice: Subject to any disclaimer, the term of this patent is extended or adjusted under 35 U.S.C. 154(b) by 164 days.

(21) Appl. No.: 14/037,750

(22) Filed: Sep. 26, 2013

(65) Prior Publication Data

US 2014/0096282 A1    Apr. 3, 2014

Related U.S. Application Data

(60) Provisional application No. 61/707,868, filed on Sep. 28, 2012.

(51) Int. Cl.
*C12N 15/82*     (2006.01)
*C07K 14/01*    (2006.01)

(52) U.S. Cl.
CPC .......... *C12N 15/8283* (2013.01); *C07K 14/01* (2013.01)

(58) Field of Classification Search
None
See application file for complete search history.

(56) References Cited

U.S. PATENT DOCUMENTS

| 2002/0138867 A1* | 9/2002 | Hanley-Bowdoin | C07K 14/005 800/278 |
| 2008/0050825 A1* | 2/2008 | Frank et al. .................. | 435/468 |
| 2008/0057563 A1* | 3/2008 | Marillonnet et al. ....... | 435/252.1 |
| 2009/0126038 A1* | 5/2009 | Van De Craen et al. .... | 800/278 |

OTHER PUBLICATIONS

Elomaa et al, Molecular Breeding (1996) vol. 2 pp. 41-50.*
Colliver et al, Plant molecular Biology (1997) vol. 35 pp. 509-522.*
Emery et al, Current Biology (2003) vol. 13 pp. 1768-1774.*
Stenger, Mol Plant Microbe Interact. (1994) vol. 7 pp. 154-157.*
Hoff et al (2009) BMC Genomics, vol. 10 pp. 1-9.*
Kim et al, Plant Mol. Bio (2007) 64: 103-112.*
APS Abstract, Jul. 2008.
Fauquet, C. M. et al., "Geminivirus strain demarcation and nomenclature", (2008) Arch Virol 153:783-821.
Hamilton, Andrew et al., "Two classes of short interfering RNA in RNA silencing", (2002) The EMBO Journal 21(17):4671-4679.
Noris, Emanuela et al., "Tomato yellow leaf curl Sardinia virus can overcome transgene-mediated RNA silencing of two essential viral genes", (2004) Journal of General Virology 85:1745-1749.
Vanitharani, R. et al., "Short interfering RNA-mediated interference of gene expression and viral DNA accumulation in cultured plant cells", (2003) PNAS 100(16):9632-9636.
Wintermantel, William M. et al., "Development of novel sources of resistance to Beet curly top virus through virus-induced gene silencing", Abstract.
Wintermantel, William M. and Laura L. Hladky, "Resistance to curly top viruses through virus induced gene silencing", Poster.
Yang, Y. et al., "Use of Tomato yellow leaf curl virus (TYLCV) Rep Gene Sequences to Engineer TYLCV Resistance in Tomato", (2004) Phytopathology 94(5):490-496.
Zhang, Peng et al., "Resistance to cassava mosaic disease in transgenic cassava expressing antisense RNAs targeting virus replication genes", (2005) Plant Biotechnology Journal 3:385-397.
Chen, L.F. et al., "Genetic diversity in curtoviruses: a highly divergent strain of Beet mild curly top virus associated with an outbreak of curly top disease in pepper in Mexico", (2011), Archives of Virology 156:547-555.
Hong, Yiguo et al., "Regulation of African cassava mosaic virus complementary-sense gene expression by N-terminal sequences of the replication-associated protein AC1", (1995), Journal of General Virology 76:2415-2422.
Hou, Yu-Ming et al., "Transgenic Plants Expressing Geminivirus Movement Proteins: Abnormal Phenotypes and Delayed Infection by Tomato mottle virus in Transgenic Tomatoes Expressing the Bean dwarf mosaic virus BV1 or BC1 Proteins", (2000), MPMI 13(3):297-308.
Krake, L.R. et al., "Expression of the Tomato Leaf Curl Geminivirus C4 Gene Produces Viruslike Symptoms in Transgenic Plants", (1998), MPMI 11(5):413-417.
Lanham et al., "Induction of plant cell division by beet curly top virus gene C4", (1997), The Plant Journal 11(6):1273-1283.
Noris, E. et al., "DNA-Binding Activity of the C2 Protein of Tomato Yellow Leaf Curl Geminivirus", (1996), Virology 217:607-612, Article No. 0157.
Strausbaugh, C.A. et al., "Curly Top Survey in the Western United States", (2008), Phytopathology 98(11):1212-1217.
Varsani, Arvind et al., "Revisiting the classification of curtoviruses based on genome-wide pairwise identity", (2014), Archives of Virology 159:1873-1882.
Yang, Y. et al., "Use of Tomato yellow leaf curl virus (TYLCV) Rep Gene Sequences to Engineer TYLCV Resistance in Tomato", (2004) Phytopathology 94:490-496.

* cited by examiner

*Primary Examiner* — Amjad Abraham
*Assistant Examiner* — Bratislav Stankovic
(74) *Attorney, Agent, or Firm* — John D. Fado; David L. Marks

(57) ABSTRACT

The disclosure provides plant vaccine compositions and methods for inducing immunity to Beet Curly Top Virus (BCTV) and related curtoviruses in a susceptible plant.

28 Claims, 3 Drawing Sheets

SEQUENCE LISTING

<160> NUMBER OF SEQ ID NOS: 17

<210> SEQ ID NO 1
<211> LENGTH: 40
<212> TYPE: DNA
<213> ORGANISM: Artificial Sequence
<220> FEATURE:
<223> OTHER INFORMATION: Primer

<400> SEQUENCE: 1
atatggatcc atttaaattt acayggyagw ttgarcttgc                     40

<210> SEQ ID NO 2
<211> LENGTH: 34
<212> TYPE: DNA
<213> ORGANISM: Artificial Sequence
<220> FEATURE:
<223> OTHER INFORMATION: Primer

<400> SEQUENCE: 2
atataagctt gttytrtata acgtcattga tgac                           34

<210> SEQ ID NO 3
<211> LENGTH: 341
<212> TYPE: DNA
<213> ORGANISM: Beet curly top virus

<400> SEQUENCE: 3
atatggatcc atttaaattt acatggcaga ttgagcttgc gaggacgctt cttgattgtt      60
atcaaagaga ggacttgtga gtttggcgaa gactgaattt tgtaatgtcc aggacctaag     120
ggcttcattt tctgatttat tgaggaagtc ctggtaagag ctgccttcgc ctggattgca     180
taatataata ctgggaatac cacctttaat gacacgtggt tttccatact ttaagtttgt     240

```
ctgccactct ctttgtgcgc ctataaggtg cttccaatgc ttcatcttta agtaatttgg      300
atctacgtca tcaatgacgt tatatagaac aagccctata t                         341
```

<210> SEQ ID NO 4
<211> LENGTH: 31
<212> TYPE: DNA
<213> ORGANISM: Artificial Sequence
<220> FEATURE:
<223> OTHER INFORMATION: Primer

<400> SEQUENCE: 4

```
atatctcgag ctytcaaaaa acggtcycca g                                     31
```

<210> SEQ ID NO 5
<211> LENGTH: 31
<212> TYPE: DNA
<213> ORGANISM: Artificial Sequence
<220> FEATURE:
<223> OTHER INFORMATION: Primer

<400> SEQUENCE: 5

```
ttaaaagctt atcasggatt ttcgcacrga r                                     31
```

<210> SEQ ID NO 6
<211> LENGTH: 270
<212> TYPE: DNA
<213> ORGANISM: Beet curly top virus

<400> SEQUENCE: 6

```
atatctcgag ctttcaaaaa acggtcccca gttaatgtcc tgtgtgctcc agtgatcgtc       60
aaatctatcc agcacttgtg aagattcaag tatttgcgga ggttgtggtt gaatcttatc      120
tggactttca gttgataaac tggcccggaa cggaagaagt cctggagttt gaggtacaat      180
ggattgggta ccaagtccac gggtatggaa ttcgtcgctt gttgcagcgt gatgggttcc      240
tccgtgcgaa aatccctgaa aagcttttaa                                      270
```

<210> SEQ ID NO 7
<211> LENGTH: 39
<212> TYPE: DNA
<213> ORGANISM: Artificial Sequence
<220> FEATURE:
<223> OTHER INFORMATION: Primer

<400> SEQUENCE: 7

```
tcattctaga ggcgcgcctg aatcctcaaa gtgcgtggc                             39
```

<210> SEQ ID NO 8
<211> LENGTH: 35
<212> TYPE: DNA
<213> ORGANISM: Artificial Sequence
<220> FEATURE:
<223> OTHER INFORMATION: Primer

<400> SEQUENCE: 8

```
atttctcgag tctctgacta tcaccaatac cctgg                                 35
```

<210> SEQ ID NO 9
<211> LENGTH: 239
<212> TYPE: DNA
<213> ORGANISM: Beet curly top virus

<400> SEQUENCE: 9

```
tcattctaga ggcgcgcctg aatcctaaag tgcgtggccg aagaagagga ggactactac      60
```
gatttcgagg aaataccaat ggaggagacc tgtgacaaaa aacaggactc tgaagttaaa    120
gatgtatgat gatatgttgg gtgctggtgg tataggatct accattagta ataatggtat    180
gattactatg ttgaataatt atgtccaggg tattggtgat agtcagagac tcgagaaat     239

<210> SEQ ID NO 10
<211> LENGTH: 764
<212> TYPE: DNA
<213> ORGANISM: Artificial Sequence
<220> FEATURE:
<223> OTHER INFORMATION: synthetic derived from beet severe curly top
      virus fragments

<400> SEQUENCE: 10
ggcgcgcctg aatcctaaag tgcgtggccg aagaagagga ggactactac gatttcgagg     60
aaataccaat ggaggagacc tgtgacaaaa acaggactc tgaagttaaa gatgtatgat    120
gatatgttgg gtgctggtgg tataggatct accattagta ataatggtat gattactatg    180
ttgaataatt atgtccaggg tattggtgat agtcagagac tcgagctttc aaaaaacggt    240
ccccagttaa tgtcctgtgt gctccagtga tcgtcaaatc tatccagcac ttgtgaagat    300
tcaagtattt gcggaggttg tggttgaatc ttatctggac tttcagttga taaactggcc    360
cggaacggaa gaagtcctgg agtttgaggt acaatggatt gggtaccaag tccacgggta    420
tggaattcgc ccttatatag gcttgttct atataacgtc attgatgacg tagatccaaa    480
ttacttaaag atgaagcatt ggaagcacct tataggcgca caaagagagt ggcagacaaa    540
cttaaagtat ggaaaaccac gtgtcattaa aggtggtatt cccagtatta tattatgcaa    600
tccaggcgaa ggcagctctt accaggactt cctcaataaa tcagaaaatg aagcccttag    660
gtcctggaca ttacaaaatt cagtcttcgc caaactcaca agtcctctct ttgataacaa    720
tcaagaagcg tcctcgcagc tcaatctgcc atgtaaattt aaat                     764

<210> SEQ ID NO 11
<211> LENGTH: 770
<212> TYPE: DNA
<213> ORGANISM: Artificial Sequence
<220> FEATURE:
<223> OTHER INFORMATION: synthetic derived from beet severe curly top
      virus fragments

<400> SEQUENCE: 11
gatccattta aatttacatg gcagattgag cttgcgagga cgcttcttga ttgttatcaa     60
agagaggact tgtgagtttg gcgaagactg aattttgtaa tgtccaggac ctaagggctt    120
cattttctga tttattgagg aagtcctggt aagagctgcc ttcgcctgga ttgcataata    180
taatactggg aataccacct ttaatgacac gtggttttcc atactttaag tttgtctgcc    240
actctctttg tgcgcctata aggtgcttcc aatgcttcat ctttaagtaa tttggatcta    300
cgtcatcaat gacgttatat agaacaagcc tatataagg gcgaattcca tacccgtgga    360
cttggtaccc aatccattgt acctcaaact ccaggacttc ttccgttccg ggccagttta    420
tcaactgaaa gtccagataa gattcaacca caacctccgc aaatacttga atcttcacaa    480
gtgctggata gatttgacga tcactggagc acacaggaca ttaactgggg accgtttttt    540
gaaagctcga gtctctgact atcaccaata ccctggacat aattattcaa catagtaatc    600
ataccattat tactaatggt agatcctata ccaccagcac ccaacatatc atcatacatc    660
tttaacttca gagtcctgtt ttttgtcaca ggtctcctcc attggtattt cctcgaaatc    720

```
gtagtagtcc tcctcttctt cggccacgca ctttaggatt caggcgcgcc          770
```

<210> SEQ ID NO 12
<211> LENGTH: 33
<212> TYPE: DNA
<213> ORGANISM: Artificial Sequence
<220> FEATURE:
<223> OTHER INFORMATION: Primer

<400> SEQUENCE: 12

```
gcatatggat cctgcagcat cattagccgt ctg                            33
```

<210> SEQ ID NO 13
<211> LENGTH: 30
<212> TYPE: DNA
<213> ORGANISM: Artificial Sequence
<220> FEATURE:
<223> OTHER INFORMATION: Primer

<400> SEQUENCE: 13

```
ccgaatccgg atttgaagag agcccgattc                                30
```

<210> SEQ ID NO 14
<211> LENGTH: 415
<212> TYPE: DNA
<213> ORGANISM: Beet curly top virus

<400> SEQUENCE: 14

```
tgcagcatca ttagccgtct gttgacctcc gcgtgcagat cttccatcga cctgaaattc    60
accccagtcg atgtgatctc cgtcctttga gacgtaggac ttgacgtcgg aactggattt   120
agctccctga atattgcagt ggaattgttt gctggtactt cgatgttgca gatcgaagta   180
acgggcatta cggatctgga cttttccttc gaattgaata agggcatgca gatgtggttc   240
cccattttca tgtaattctc tgcagatgcg aatatatttt ttattcgaag gtgtatttat   300
agcgaggagc tgttctaagg cgtcttcttt ggttactgaa cattgagggt atgtaaggaa   360 aaaattttg gctttttttgt aaaaaggcat attgaatcgg gctctcttca aatcc        415
```

<210> SEQ ID NO 15
<211> LENGTH: 32
<212> TYPE: DNA
<213> ORGANISM: Artificial Sequence
<220> FEATURE:
<223> OTHER INFORMATION: Primer

<400> SEQUENCE: 15

```
gatcggattc ttacayggya gwttgarctt gc                             32
```

<210> SEQ ID NO 16
<211> LENGTH: 34
<212> TYPE: DNA
<213> ORGANISM: Artificial Sequence
<220> FEATURE:
<223> OTHER INFORMATION: Primer

<400> SEQUENCE: 16

```
gatcccatgg gttytrtata acgtcattga tgac                           34
```

<210> SEQ ID NO 17
<211> LENGTH: 312
<212> TYPE: DNA
<213> ORGANISM: Beet curly top virus

<400> SEQUENCE: 17

-continued

```
ttacaaggaa gtttgatctt gcgaggacgc ttcttgattg ttatcaaaga gaggacttgt     60
gagtttggcg aagactgaat tttgtaatgt ccaggaccta agggcttcat tttctgattt    120
attgaggaag tcctggtaag agctgccttc gcctggattg cataatataa tactgggaat    180
accaccttta atgacacgtg gttttccata ctttaagttt gtctgccact ctctttgtgc    240
gcctataagg tgcttccaat gcttcatctt taagtaattg ggatctacgt catcaatgac    300
gttatacaga ac                                                        312
```

US 9,556,452 B2

VACCINE FOR CONTROL OF BEET CURLY TOP VIRUS INFECTION OF PLANTS

REFERENCE TO RELATED APPLICATIONS

This application claims priority to U.S. Provisional Patent Application Ser. No. 61/707,868, filed Sep. 28, 2012, which is incorporated herein by reference in its entirety.

FIELD OF THE INVENTION

The invention relates to virus-induced gene silencing in plants.

BACKGROUND OF THE INVENTION

Curly top disease, is caused by Beet curly top virus (BCTV) and related viruses in the genus *Curtovirus*, family Geminiviridae. BCTV severely impacts vegetable, dry bean, and sugar beet production throughout large portions of the western United States from e.g., California and Oregon to Texas, Oklahoma, and Nebraska. Transmitted by the beet leafhopper, *Circulifer tenellus*, the virus infects a broad host range from many plant families causing disease in over 300 species in 44 plant families.

The virus is typically restricted to broad-leafed plants, as no monocotyledonous plants have been identified as hosts for this virus. The most commonly infected hosts include sugar beets (for which the disease was first named), tomatoes, peppers, beans, potatoes, spinach, cucurbits, cabbage, alfalfa, and many ornamentals. The virus also survives in many weeds, such as Russian thistle (tumbleweed) and mustard.

The wide host range of curtoviruses, the abundance of the beet leafhopper, and increasing acreage of uncultivated rangeland where weeds (e.g., tumble weed) are allowed to grow unchecked are making curly top management increasingly difficult.

For over a century management of curly top disease in the western United States has focused on the large-scale application of insecticides to beet leafhopper over-wintering grounds, as well as insecticide application to crops in efforts to reduce populations of the leafhopper vector. Unfortunately, since leafhopper transmission of curtoviruses requires only a brief feeding interval to introduce the virus into a healthy plant, treating e.g., sugarbeet plantings with insecticides does not effectively block virus all virus transmission. Furthermore, insecticide application has potential for unintended negative biological and environmental consequences.

Resistance to curly top has been identified in a select number of crops, but unfortunately, none of these eliminate the ability of the virus to infect, and some resistant crops exhibit non-desirable traits that are difficult to separate through plant breeding.

Therefore, what is needed in the art are effective means to control beet curly top virus. Fortunately, as will be clear from the following disclosure, the present invention provides for these and other needs.

SUMMARY OF THE INVENTION

In an exemplary aspect, the disclosure provides a plant vaccine composition for inducing immunity to Beet Curly Top Virus (BCTV) and related curtovirus species in a susceptible plant, the plant vaccine comprising: an expression vector comprising an isolated BCTV vaccine nucleic acid sequence that is a member selected from the group consisting of nucleic acid sequences having at least about 90% sequence identity to SEQ ID NO: 10, at least about 90% sequence identity SEQ ID NO:14 and at least about sequence identity 90% SEQ ID NO:17, operably linked to a promoter sequence. In one exemplary embodiment, the expression vector comprises an isolated BCTV vaccine nucleic acid sequence that is a member selected from the group consisting of nucleic acid sequences having at least about 95% sequence identity to SEQ ID NO:10, at least about 95% sequence identity to SEQ ID NO:14 and at least about 95% sequence identity to SEQ ID NO:17, operably linked to a promoter sequence. In another exemplary embodiment, the expression vector comprises an isolated BCTV vaccine nucleic acid sequence that is a member selected from the group consisting of nucleic acid sequences having at least about 99% sequence identity to SEQ ID NO:10, at least about 99% sequence identity to SEQ ID NO:14 and at least about 99% sequence identity to SEQ ID NO:17, operably linked to a promoter sequence. In another exemplary embodiment, the expression vector comprises an isolated BCTV vaccine nucleic acid sequence that is a member selected from the group consisting of SEQ ID NO:10, SEQ ID NO:14 and SEQ ID NO:17, operably linked to a promoter sequence. In another exemplary embodiment, the expression vector comprises an isolated BCTV vaccine nucleic acid sequence that forms a hairpin structure, wherein the isolated BCTV vaccine nucleic acid sequence that forms a hairpin structure consists essentially of smaller BCTV vaccine nucleic acid sequences that are arranged sequentially to form the isolated BCTV vaccine nucleic acid sequence that forms a hairpin structure, wherein the smaller BCTV vaccine nucleic acid sequences are arranged so that a first sequence having at least about 99% sequence identity to SEQ ID NO:10 is placed next to a second sequence consisting of an intron, and the intron is placed next to a third sequence having at least about 99% sequence identity to SEQ ID NO:11, wherein the isolated BCTV vaccine nucleic acid sequence that forms a hairpin structure is operably linked to a promoter sequence. In another exemplary embodiment, the vaccine induces immunity to Beet Curly Top Viruses that are members selected from the group consisting of beet severe curly top virus (BSCTV) and beet mild curly top virus (BMCTV). In another exemplary embodiment, the susceptible plant is a member selected from the group consisting of sugar beet (*Beta vulgaris*), tomato (*solanum lycopersicum*), bean (*Phaseolus vulgaris*), and pepper (*Capsicum* spp.). In another exemplary embodiment, the susceptible plant is sugar beet. In another exemplary embodiment, the susceptible plant is tomato.

In another exemplary aspect, the disclosure provides a method for inducing immunity to Beet Curly Top Virus (BCTV) and related curtovirus species in a susceptible plant, thereby protecting the susceptible plant from infection with BCTV and related curtovirus species, the method comprising: (i) transfecting the susceptible plant with a suspension of *Agrobacterium tumefaciens* to provide a vaccinated plant, wherein the *Agrobacterium tumefaciens* comprises a plant vaccine that comprises an expression vector comprising an isolated BCTV vaccine nucleic acid sequence that is a member selected from the group consisting of nucleic acid sequences having at least about 90% sequence identity to SEQ ID NO: 10, at least about 90% sequence identity SEQ ID NO:14 and at least about sequence identity 90% SEQ ID NO:17, operably linked to a promoter sequence, wherein expression of the isolated BCTV vaccine nucleic acid sequence in the vaccinated plant induces transient silencing of the BCTV and related curtovirus species, thereby protecting the susceptible plant from infection with BCTV and related curtovirus species. In an exemplary embodiment, the isolated BCTV vaccine nucleic acid sequence is a member selected from the group consisting of nucleic acid sequences having at least about 95% sequence identity to SEQ ID NO:10, at least about 95% sequence identity to SEQ ID NO:14 and at least about 95% sequence identity to SEQ ID NO:17, operably linked to a promoter sequence. In another exemplary embodiment, the isolated BCTV vaccine nucleic acid sequence is a member selected from the group consisting of the group consisting of nucleic acid sequences having at least about 99% sequence identity to SEQ ID NO:10, at least about 99% sequence identity to SEQ ID NO:14 and at least about 99% sequence identity to SEQ ID NO:17, operably linked to a promoter sequence. In another exemplary embodiment, the isolated BCTV vaccine nucleic acid sequence is a member selected from the group consisting of SEQ ID NO:10, SEQ ID NO:14 and SEQ ID NO:17. In another exemplary embodiment, the isolated BCTV vaccine nucleic acid sequence forms a hairpin structure, wherein the isolated BCTV vaccine nucleic acid sequence that forms a hairpin structure consists essentially of smaller BCTV vaccine nucleic acid sequences that are arranged sequentially to form the isolated BCTV vaccine nucleic acid sequence that forms a hairpin structure, wherein the smaller BCTV vaccine nucleic acid sequences are arranged so that a first sequence having at least about 99% sequence identity to SEQ ID NO:10 is placed next to a second sequence consisting of an intron, and the intron is placed next to a third sequence having at least about 99% sequence identity to SEQ ID NO:11, wherein the isolated BCTV vaccine nucleic acid sequence that forms a hairpin structure is operably linked to a promoter sequence. In another exemplary embodiment, the transfection is transient transfection. In another exemplary embodiment, transient transfection is carried out by direct injection of the suspension of *Agrobacterium tumefaciens* into a stem of the susceptible plant. In another exemplary embodiment, the transient transfection is carried out by airbrushing the suspension of *Agrobacterium tumefaciens* into one or more leaves of the susceptible plant. In another exemplary embodiment, the method induces immunity to Beet Curly Top Viruses that are members selected from the group consisting of beet severe curly top virus (BSCTV) and beet mild curly top virus (BMCTV). In another exemplary embodiment, the susceptible plant is a member selected from the group consisting of sugar beet (*Beta vulgaris*), tomato (*solanum lycopersicum*), bean (*Phaseolus vulgaris*), and pepper (*Capsicum* spp.). In another exemplary embodiment, the susceptible plant is sugar beet. In another exemplary embodiment, the susceptible plant is tomato.

Other features, objects and advantages of the invention will be apparent from the detailed description which follows.

DETAILED DESCRIPTION OF THE INVENTION

Definitions

Figure 1:
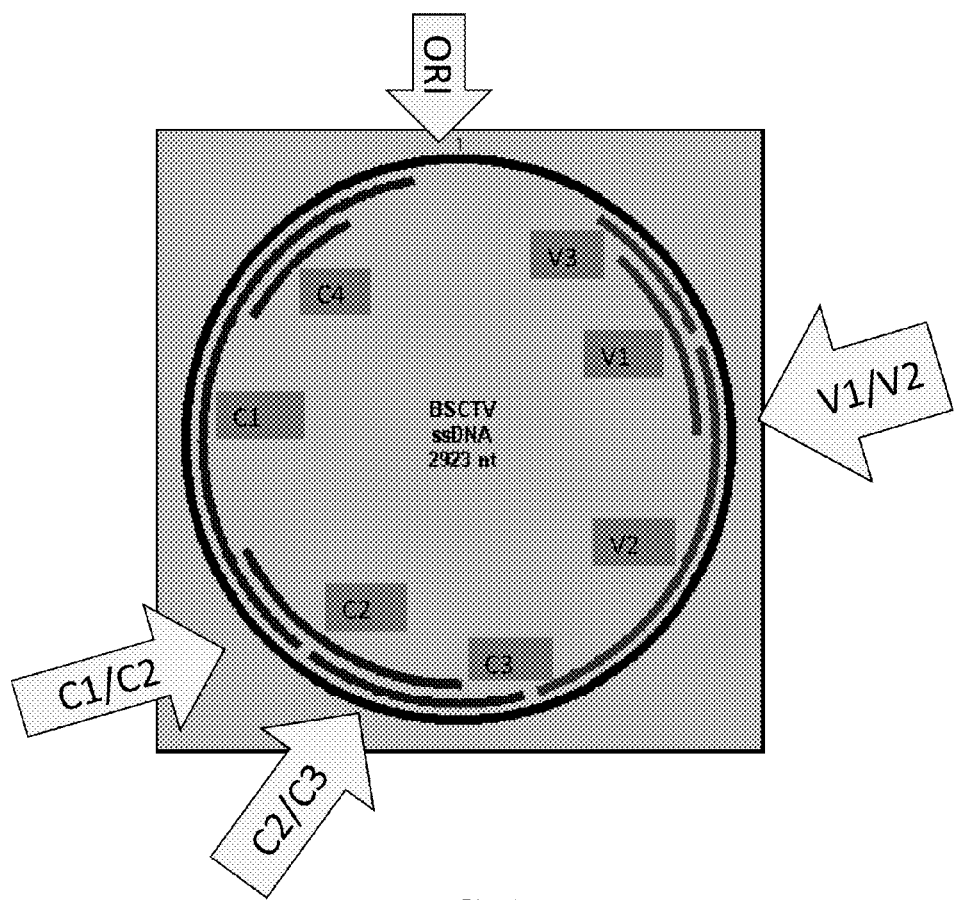
FIG. 1. Illustrates the genomic organization of Beet severe curly top virus (BSCTV) and is generally representative of the genomes of other curtoviruses, including BMCTV, BCTV, and others.

The term "plant" as used herein refers to whole plants, plant bodies, plant organs (e.g., leaves, stems, flowers, roots, etc.), seeds, plant tissues, plant cells and progeny of same. In an exemplary embodiment, a plant cell includes callus. In another exemplary embodiment, a plant organ includes a root, a leaf, a flower and/or the like. The term "plant" refers to the broad class of higher plants amenable to transformation techniques. The term "plant" also includes monocotyledonous and dicotyledonous plants, plants of any variety of ploidy levels, including polyploid, diploid, haploid and hemizygous.

Some exemplary plants include, but are not limited, to sugar beet (*Beta vulgaris*), bean (*Phaseolus vulgaris*), pepper (*Capsicum* ssp), tomato (*Solanum lycopersicum*), potato (*Solanum tuberosum*), members of the genus *Cucurbita* e.g., Hubbard squash (*C. Hubbard*), Butternut squash (*C. moschtata*), Zucchini (*C. pepo*), Crookneck squash (*C. crookneck*), *C. argyrosperma, C. argyrosperma* ssp *sororia, C. digitata, C. ecuadorensis, C. foetidissima, C. lundelliana,* and *C. martinezii*, and members of the genus *Cucumis* such as cucumber (*Cucumis sativus*), cantaloupe (*C. cantalupensis*), and musk melon (*C. melo*). Ornamental plants e.g., azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherima*), cabbage, *Arabidopsis*, etc.

The term "transgenic plant" as used herein refers to a plant comprising at least one heterologous nucleic acid sequence that was introduced into the plant, at some point in its lineage, by genetic engineering techniques. In an exemplary embodiment, a transgenic plant is a plant that is the progeny or decendant of a plant that is transformed with at least one heterologous nucleic acid sequence and which comprises heterologous nucleic acid. Thus, the term "transgenic plant" refers to plants which are the direct result of transformation with a heterologous nucleic acid or transgene, and the progeny and decendants of transformed plants which comprise the introduced heterologous nucleic acid or transgene.

The expression "isolated BCTV vaccine nucleic acid" "isolated BCTV vaccine nucleic acid sequence" or "isolated BCTV vaccine sequence" as used herein, refers to isolated BCTV vaccine nucleic acids which comprise a nucleotide sequence identical to or substantially identical to SEQ ID NO:10, SEQ ID NO:14 or SEQ ID NO:17 and which are able to induce immunity to beet curly top virus (BCTV) in plants.

An exemplary isolated BCTV vaccine nucleic acid consists essentially of a nucleotide sequence as shown in SEQ ID NO:10 or segment or fragment thereof. In one exemplary embodiment, an "isolated BCTV vaccine nucleic acid sequence" refers to an isolated nucleotide sequence identical to or substantially identical to SEQ ID NO:14 or segment or fragment thereof or an isolated nucleic acid identical to or substantially identical to SEQ ID NO:17 or segment or fragment thereof, and which are able to induce immunity to beet curly top virus (BCTV) and related curtoviruses in susceptible plants. Thus, an exemplary isolated BCTV vaccine sequence is SEQ ID NO:10. Another exemplary isolated BCTV vaccine sequence is SEQ ID NO:14. Still another exemplary isolated sequence is illustrated as SEQ ID NO:17. Typically, isolated BCTV vaccine sequences are derived from specific nucleic acid segments derived from BCTV genome as disclosed hereinbelow. However, isolated BCTV vaccine sequences can be isolated from any source and/or can be synthetically made, by methods known on the art (see e.g., U.S. Pat. No. 5,942,609) as long as they are substantially identical to isolated BCTV vaccine nucleic acid sequences as disclosed herein. Methods for determining nucleotide sequence identity and "substantial identity" are described below. However, in general, two nucleic acid sequences are considered to be substantially identical when the two molecules or their complements hybridize to each other under stringent hybridization conditions, as described below.

The expression "isolated BCTV nucleic acid" or "isolated BCTV sequence" or other grammatically equivalent expressions as used herein, refer to isolated BCTV nucleic acids derived from any known BCTV genomic sequence e.g., derived from Beet severe curly top virus (BSCTV; GenBank Accession Number NC_004754) Beet mild curly top virus (BMCTV; NC_004753) Beet curly top virus (BCTV; NC_001412). Thus, in an exemplary embodiment, a BCTV vaccine sequence comprises segments or fragments of isolated BCTV nucleic acids.

The terms "isolated," "purified," or "biologically pure" as used herein, refer to material that is substantially or essentially free from components that normally accompany it as found in its native state. In an exemplary embodiment, purity and homogeneity are determined using analytical chemistry techniques such as polyacrylamide gel electrophoresis or high performance liquid chromatography. A nucleic acid that is the predominant species present in a preparation is substantially purified. In one exemplary embodiment, an isolated BCTV vaccine nucleic acid is separated from open reading frames and/or other nucleic acid sequences that flank the isolated BCTV vaccine nucleic acid in its native state. In an exemplary embodiment, the term "purified" denotes that a nucleic acid or protein gives rise to essentially one band in an electrophoretic gel. Typically, isolated nucleic acids or proteins have a level of purity expressed as a range. The lower end of the range of purity for the component is about 60%, about 70% or about 80% and the upper end of the range of purity is about 70%, about 80%, about 90% or more than about 90%.

The term "nucleic acid" as used herein, refers to a polymer of ribonucleotides or deoxyribonucleotides. Typically, "nucleic acid" polymers occur in either single- or double-stranded form, but are also known to form structures comprising three or more strands. The term "nucleic acid" includes naturally occurring nucleic acid polymers as well as nucleic acids comprising known nucleotide analogs or modified backbone residues or linkages, which are synthetic, naturally occurring, and non-naturally occurring, which have similar binding properties as the reference nucleic acid, and which are metabolized in a manner similar to the reference nucleotides. Exemplary analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (see e.g., Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

The terms "polypeptide," "peptide" and "protein" are used interchangeably herein to refer to a polymer of amino acid residues. The terms apply to naturally occurring amino acid polymers and non-naturally occurring amino acid polymers as well as amino acid polymers in which one or more amino acid residues is an artificial chemical mimetic of a corresponding naturally occurring amino acid.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, 7-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids are referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art (see, e.g., Creighton, Proteins (1984)). Such conservatively modified variants are in addition to and do not exclude polymorphic variants, interspecies homologs, and alleles.

The following eight groups illustrate some exemplary amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

Macromolecular structures such as polypeptide structures are described in terms of various levels of organization. For a general discussion of this organization, see, e.g., Alberts et al., Molecular Biology of the Cell ($3^{rd}$ ed., 1994) and Cantor and Schimmel, Biophysical Chemistry Part I: The Conformation of Biological Macromolecules (1980). "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 50 to 350 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

The term "label" as used herein, refers to a composition detectable by spectroscopic, photochemical, biochemical, immunochemical, or chemical means. Exemplary labels include $^{32}P$, fluorescent dyes, electron-dense reagents, enzymes (e.g., as commonly used in an ELISA), biotin, digoxigenin, or haptens and proteins for which antisera or monoclonal antibodies are available.

As used herein a "nucleic acid probe or oligonucleotide" refers to a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (e.g., 7-deazaguanosine, inosine, etc.). In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. In one exemplary embodiment, probes are directly labeled as with isotopes, chromophores, lumiphores, chromogens etc. In other exemplary embodiments probes are indirectly labeled e.g., with biotin to which a streptavidin complex may later bind. By assaying for the presence or absence of the probe, one can detect the presence or absence of the select sequence or subsequence.

Thus, the term "labeled nucleic acid probe or oligonucleotide" as used herein refers to a probe that is bound, either covalently, through a linker or a chemical bond, or noncovalently, through ionic, van der Waals, electrostatic, or hydrogen bonds to a label such that the presence of the probe may be detected by detecting the presence of the label bound to the probe.

The term "primer" as used herein, refers to short nucleic acids, typically DNA oligonucleotides of at least about 15 nucleotides in length. In an exemplary embodiment, primers are annealed to a complementary target DNA strand by nucleic acid hybridization to form a hybrid between the primer and the target DNA strand. Annealed primers are then extended along the target DNA strand by a DNA polymerase enzyme. Primer pairs can be used for amplification of a nucleic acid sequence, e.g., by the polymerase chain reaction (PCR) or other nucleic-acid amplification methods known in the art.

PCR primer pairs are typically derived from a known sequence, for example, by using computer programs intended for that purpose such as Primer (Version 0.5©1991, Whitehead Institute for Biomedical Research, Cambridge, Mass.). One of skill in the art will appreciate that the specificity of a particular probe or primer increases with its length. Thus, for example, a primer comprising 20 consecutive nucleotides of an isolated BCTV vaccine sequence will anneal to a related target sequence with a higher specificity than a corresponding primer of only 15 nucleotides. Thus, in an exemplary embodiment, greater specificity of a nucleic acid primer or probe, is attained with probes and primers selected to comprise 20, 25, 30, 35, 40, 50 or more consecutive nucleotides of a selected sequence.

Nucleic acid probes and primers are readily prepared based on the nucleic acid sequences disclosed herein. Methods for preparing and using probes and primers and for labeling and guidance in the choice of labels appropriate for various purposes are discussed, e.g., in Sambrook et al., *Molecular Cloning, A Laboratory Manual* 2nd ed. 1989, Cold Spring Harbor Laboratory; and *Current Protocols in Molecular Biology*, Ausubel et al., eds., 1994, John Wiley & Sons). The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, over expressed, under expressed or not expressed at all.

The term "promoter" or "promoter complex" or "promoter sequence" as used herein refers to an array of nucleic acid expression control sequences that direct transcription of a nucleic acid. As used herein, a "promoter" or "promoter complex" or "promoter sequence" comprises necessary nucleic acid sequences near the start site of transcription, such as, e.g., a polymerase II type promoter, a TATA element etc to "control" transcription of an operably linked nucleic acid. In some exemplary embodiments, a "promoter complex" or "promoter sequence" also includes distal enhancer or repressor elements, which can be, but are not necessarily located as much as several thousand base pairs from the start site of transcription. In other exemplary embodiments, "promoter" or "promoter complex" or "promoter sequence" includes sequences that facilitate transcription of an operably linked heterologous nucleic acid and/or expression of the final protein or nucleic acid product of the heterologous nucleic acid e.g., BCTV vaccine sequences as disclosed herein.

The term "capable of hybridizing under stringent hybridization conditions" as used herein, refers to annealing a first nucleic acid to a second nucleic acid under stringent hybridization conditions (defined below). In an exemplary embodiment, the first nucleic acid is a test sample, and the second nucleic acid is the sense or antisense strand of an isolated BCTV nucleic acid. Hybridization of the first and second nucleic acids is conducted under standard stringent conditions, e.g., high temperature and/or low salt content, which tend to disfavor hybridization of dissimilar nucleotide sequences.

The term "operably linked" refers to a functional linkage between a nucleic acid expression control sequence (such as e.g., an isolated curtovirus nucleic acid, or array of transcription factor binding sites) and a second nucleic acid sequence, wherein the expression control sequence directs expression e.g., transcription, of the nucleic acid corresponding to the second sequence. In an exemplary embodiment, a promoter e.g., an isolated curtovirus nucleic acid, that is "operably linked" to a heterologous nucleic acid is located upstream of and in-frame with the heterologous nucleic acid.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

An "expression cassette" as used herein, refers to a nucleic acid construct, typically generated recombinantly or synthetically, which comprises a series of specified nucleic acid elements that permit transcription of a particular nucleic acid in a host cell. In an exemplary embodiment, an expression cassette comprises a heterologous nucleic acid to be transcribed e.g., a BCTV vaccine nucleic acid, operably linked to a promoter.

Typically, an "expression cassette" is part of an "expression vector". The term "vector" as used herein, refers to nucleic acid capable of replicating in a selected host cell or organism. A vector can replicate as an autonomous structure, or alternatively can integrate into the host cell chromosomes and thus replicate along with the host cell genome. Thus, an "expression vector" is a nucleic acid capable of replicating in a selected host cell or organism e.g., a plasmid, virus, artificial chromosome, nucleic acid fragment, or any suitable construct known in the art, which comprises an "expression cassette".

The term "transformation" or "transfection" are used interchangeably herein and encompasses any and all techniques by which a nucleic acid molecule might be introduced into a cell, including but not limited to, transfection with viral vectors, transformation with plasmid vectors, and introduction of naked DNA by electroporation, lipofection, *Agrobacterium* infection, and particle gun acceleration.

The following terms are used to describe the sequence relationships between two or more nucleic acids or polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length isolated BCTV vaccine sequence or gene sequence given in a sequence listing, or may comprise a complete isolated BCTV vaccine sequence or gene sequence.

The terms "identical" or percent "identity," in the context of two or more nucleic acids or polypeptide sequences, refer to two or more sequences or subsequences that are the same or have a specified percentage of amino acid residues or nucleotides that are the same (e.g., 85% identity, 90% identity, 99%, or 100% identity), when compared and aligned for maximum correspondence over a comparison window, or designated region as measured using a sequence comparison algorithm or by manual alignment and visual inspection.

The phrase "substantially identical", in the context of two nucleic acids or polypeptides, refers to two or more sequences or subsequences that have at least about 85%, identity, at least about 86%, 87%, 88%, 89%, 90%, 91%, 92%, 93%, 94%, 95%, 96%, 97%, 98%, 99%, or 100% nucleotide or amino acid residue identity, when compared and aligned for maximum correspondence, as measured using a sequence comparison algorithm or by visual inspection. In an exemplary embodiment, the substantial identity exists over a region of the sequences that is at least about 50 residues in length. In another exemplary embodiment, the substantial identity exists over a region of the sequences that is at least about 100 residues in length. In still another exemplary embodiment, the substantial identity exists over a region of the sequences that is at least about 150 residues or more, in length. In one exemplary embodiment, the sequences are substantially identical over the entire length of nucleic acid or protein sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

An exemplary algorithm for sequence comparason is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, J. Mol. Evol. 35:351-360 (1987). The method used is similar to the method described by Higgins & Sharp, CABIOS 5:151-153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., Nuc. Acids Res. 12:387-395 (1984).

Another example of algorithm that is suitable for determining percent sequence identity and sequence similarity are the BLAST and BLAST 2.0 algorithms, which are described in Altschul et al., Nuc. Acids Res. 25:3389-3402 (1977) and Altschul et al., J. Mol. Biol. 215:403-410 (1990), respectively. Software for performing BLAST analyses is publicly available through the National Center for Biotechnology Information (ncbi.nlm.nih.gov). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N4 and a comparison of both strands. For amino acid sequences, the BLASTP program uses as defaults a wordlength of 3, and expectation (E) of 10, and the BLOSUM62 scoring matrix (see Henikoff & Henikoff, Proc. Natl. Acad. Sci. USA 89:10915 (1989)) alignments (B) of 50, expectation (E) of 10, M=5, N=4, and a comparison of both strands.

The BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA). In general, two nucleic acid sequences are said to be "substantially identical" when the two molecules or their complements selectively or specifically hybridize to each other under stringent conditions.

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology-Hybridization with Nucleic Probes, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For high stringency hybridization, a positive signal is at least two times background, preferably 10 times background hybridization. Exemplary high stringency or stringent hybridization conditions include: 50% formamide, 5×SSC and 1% SDS incubated at 42° C. or 5×SSC and 1% SDS incubated at 65° C., with a wash in 0.2×SSC and 0.1% SDS at 65° C. However, other high stringency hybridization conditions known in the art can be used.

Nucleic acids that do not hybridize to each other under stringent conditions are still substantially identical if the polypeptides that they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

I. Introduction:

Beet curly top virus (BCTV) is the most widespread geminivirus in the United States. It is endemic in the West, causing economic damage to a wide variety of crops. In the USA, the *Curtovirus* group consists essentially of seven viruses—Beet curly top virus (BCTV), Beet mild curly top virus (BMCTV), Beet severe curly top virus (BSCTV), Pepper curly top virus (PCTV), Pepper yellow dwarf virus (PYDV), Spinach curly top virus (SCTV) and Horseradish curly top virus (HrCTV). When more than one of these viruses infects a plant, they can readily exchange genes and recombine, so variation in their incidence is common, and a considerable degree of sequence variation can exist among viruses within the genus curtovirus and within the individual curtovirus species listed above.

Beet leafhoppers (*Circulifer tennellus*) are the primary vectors that transmit BCTV and other curtovirus species from plant-to-plant in North America. Other leafhopper species can transmit curtoviruses in other parts of the world. Leafhoppers typically survive throughout the year in weeds and field crops. When weeds dry out and susceptible crops e.g., sugarbeets, spinach, are planted, leafhoppers migrate from drying vegetation and weeds to irrigated agricultural fields to feed on young green tissue of the susceptible crops. Beet acquire the virus while feeding on the phloem of infected plants. The virus is ingested and moves from the digestive system to salivary glands. When the leafhoppers feed on a non-infected plant, the virus is injected with saliva into the plant. The virus is transmitted in a persistent manner, which means that leafhoppers are able to transmit the virus for the rest of their lives. However, the virus does not replicate in the leafhopper and is not passed on to the offspring (see e.g., Soto and Gilbertson, (2003) Phytopathology 93: 478-484).

Although direct feeding by beet leafhopper causes relatively minor crop damage, Beet curly top virus is extremely destructive disease of sugarbeet as well as other crops (e.g., tomatoes). Indeed, the leaves of plants infected with this virus are dwarfed, crinkled, and rolled upward and inward. Veins are roughened and often swollen. Roots become distorted, often with a proliferation of hair roots (not to be confused with Rhizomania). Phloem tissue often becomes necrotic and appears as dark rings in cross sections or dark streaks in longitudinal sections of the root. Thus, BCTV is a devastating crop pest.

To combat BCTV farm managers have employed insecticides and pesticides and weed control. Unfortunately, since transmission of BCTV requires only a brief feeding interval by leafhoppers, insecticides are not entirely effective at blocking transmission and spread of the virus. Furthermore, pesticide use on food crops is undesirable and many farm managers are making efforts to reduce pesticide usage. Thus, what is needed in the art are new and effective methods for controlling BCTV.

Numerous efforts at developing traditional host plant resistance have been attempted in several crops including bean, sugarbeet, and tomato. In sugarbeet, host plant resistance involves several genes and is difficult to move among breeding lines. Furthermore, the seed industry has been unable to separate curly top resistance from a propensity for lower than desired yields. Therefore, locations in which growers are forced to grow sugarbeets with host plant resistance (sugarbeet genes that reduce severity of curly top) cannot achieve the yields even with resistant beets that are possible in areas where curly top is not a problem. Some sources of natural resistance were developed in tomato several years ago, however, those sources were also not deemed suitable for commercialization by the tomato seed industry.

One serious obstacle to commercial development of resistance to curly top is the cost of developing a genetically modified crop. The limited number of genetically modified crops on the market required a long and extensive approval process and required far more testing and legal expenses than would be necessary for host plant resistance.

Therefore, in an exemplary embodiment, the invention provides a plant vaccine that protects crops from infection with BCTV and related curtoviruses which does not permanently alter the genetic makeup of the plant. The vaccine is administered to susceptible plants by treating said plants with a suspension of *Agrobacterium tumefaciens* containing a construct that induces transient silencing of the primary BCTV (e.g., Beet severe curly top virus (BSCTV), Beet mild curly top virus (BMCTV), and Beet curly top virus (BCTV)) affecting agriculture in the United States. In an exemplary embodiment, plants are treated as seedlings with a genetic construct that induces specific elimination of virus RNA.

In exemplary embodiments, plants are transiently transfected by direct injection into the stem, or by spraying a suspension of *A. tumefaciens* containing the genetic construct necessary to induce silencing onto the leaves of the plant treated plants. Transiently transfected plants are subsequently rinsed to wash away the delivery agent (*A. tumefaciens*), and transplanted to the field. Unlike traditional biotechnology approaches, treated plants are not permanently modified genetically.

Without being bound by theory, it is believed that administration of the vaccine stimulates the plants own "immune system" to reject the BCTV and prevent infection of the whole plant, thereby controlling BCTV. The "immune system" employs virus-induced gene silencing (VIGS), which is triggered in plants upon infection by viruses. VIGS causes selective, specific degradation of viral genome sequences, as well as any additional sequences inserted into it (see e.g., Voinnet, et al. EMBO J. 2002 September 2; 21(17): 4671-4679). VIGS can initiate even in the first cell the virus infects, preventing whole plant infection, and can be transmitted systemically throughout the plant. Although gene silencing is known primarily in the context of RNA viruses, silencing also can be effective for control of DNA viruses (see e.g., Vanitharani et al., PNAS (2003) 100(16): 9632; Yang, et al. 2004: Phytopathology 94: 490-496; Abhary et al., 2006 Arch. Virol. 151: 2349-2363).

Although gene silencing is known primarily in the context of RNA viruses, a limited number of examples have shown that silencing also can be effective for control of DNA viruses (see e.g., Vanitharani et al., PNAS (2003) supra; Yang, et al. 2004: supra; Abhary et al., 2006 supra). There are numerous examples of RNA viruses for which gene silencing based control was effectively demonstrated as a means of control. This is not the case with DNA viruses, which like higher organisms, use RNA only for expression of virus encoded proteins, and in limited cases (retroviruses and pararetroviruses) for virus replication. Furthermore, there is considerable genetic variability within the family Geminiviridae, which has resulted in separation of the family in to multiple genera based on genetic and biological variation among viruses. Demonstration of a method to induce gene silencing for one genus cannot be guaranteed to work on others, in part due to structural and functional differences among the diverse viruses within the family (Fauquet et al. 2008, Geminivirus strain demarcation and nomenclature. Arch Virol 153: 783-82E), as well as the limited studies that have been conducted on gene silencing for control of DNA viruses in plants in general.

*Curtoviruses*, like other members of the family Geminiviridae, exist almost exclusively as DNA. The virus genome is single-stranded DNA, and the virus replicates by a unique method known as rolling circle replication, using viral DNA as the template for replication (Stenger et al., 1991; PNAS 88: 8029-8033). The only point at which RNA is produced is for expression of virus encoded proteins, which are necessary for normal virus function in the host plant cell, as well as for acquisition and transmission by leafhopper vectors (reviewed in Geminiviruses (Geminiviridae); Encyclopedia of Virology, $2^{nd}$ Ed., Granoff & Webster, Eds., Academic Press, San Diego, Calif. 1999. pp 597-606). Consequently, choosing to use RNA silencing for control of curtoviruses was a bit of a risk. Very few studies have examined silencing-based control of curtoviruses, and even fewer have examined this at the whole plant level as was done here.

Studies examining gene silencing as a means of control for viruses in the family Geminiviridae usually focus on the ability to induce silencing in individual cells (see e.g., Vanitharani et al., (2003) PNAS 100: 9632-9636). Some examples have extended this resistance to whole plants, with the primary examples of this in the family Geminiviridae occurring for whitefly-transmitted viruses in the genus *Begomovirus*, particularly Tomato yellow leaf curl virus (TYLCV) and African cassava mosaic virus (ACMV) for which a few laboratories have explored biotechnology-based gene silencing as a means of control (see e.g., Yang, et al. 2004: Phytopathology 94: 490-496; Abhary et al., 2006 Arch. Virol. 151: 2349-2363; Zhang et al., 2005: Plant Biotech. J. 3: 385-397). Although studies suggest this method may be able to reduce TYLCV levels in tomato there is insufficient information to assume related viruses within the genus *Begomovirus* can be controlled with similar approaches, and virtually no information for more distantly related viruses in the genus *Curtovirus*. Furthermore, some studies have shown an ability of resistance based on a single portion of the TYLCV genome to be overcome by the virus which was to be controlled (see e.g., Noris et al., 2004; J. Gen. virol. 85: 1745-1749). TYLCV, family Geminiviridae, genus *Begomovirus*, is genetically distinct from Beet curly top virus and related species (Family Geminiviridae, Genus *Curtovirus*), as the genomes of TYLCV exhibit some differences (reviewed in Geminiviruses (Geminiviridae); Encyclopedia of Virology, $2^{nd}$ Ed., Granoff & Webster, Eds., Academic Press, San Diego, Calif. 1999. pp 597-606). No other studies have been published showing effective reduction of curtovirus concentration in plants and decreased symptom development using a gene silencing approach.

The economic significance of curly top disease to the tomato and sugar beet industries in the United States, lack of effective and/or environmentally acceptable insecticide-based control of the leafhopper vector, lack of commercially acceptable natural resistance in these crops, as well as significant impact on numerous other crops warranted aggressive efforts to determine if gene silencing-based control could effectively reduce severity of curly top by preventing infection by BCTV and other curtoviruses.

In another exemplary embodiment, stably transfected plants are prepared by dipping of seedlings in a suspension for plant transformation. There are three delivery methods: stem injection, spraying leaves and dipping of seedlings in a suspension.

II. Isolating *Curtovirus* Nucleic Acids and Constructing Expression Vectors

A. General Recombinant DNA Methods

This invention utilizes routine techniques in the field of recombinant genetics. Basic texts disclosing the general methods of use in this invention include Sambrook et al., Molecular Cloning—A Laboratory Manual (2nd Ed.), Vol. 1-3, Cold Spring Harbor Laboratory, Cold Spring Harbor, N.Y., 1989; Kriegler, Gene Transfer and Expression: A Laboratory Manual (1990); and Current Protocols in Molecular Biology (Ausubel et al., eds., 1994)). Unless otherwise noted, technical terms are used according to conventional usage. Definitions of common terms in molecular biology maybe found in e.g., Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

For nucleic acids, sizes are given in either kilobases (kb) or base pairs (bp). Estimates are typically derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized e.g., according to the solid phase phosphoramidite triester method first described by Beaucage & Caruthers, Tetrahedron Letts. 22:1859-1862 (1981), using an automated synthesizer, as described in Van Devanter et al., Nucleic Acids Res. 12:6159-6168 (1984). Purification of oligonucleotides is by either native acrylamide gel electrophoresis or by anion-exchange HPLC as described in Pearson & Reanier, J. Chrom. 255:137-149 (1983).

The sequence of the cloned genes and synthetic oligonucleotides can be verified after cloning using, e.g., the chain termination method for sequencing double-stranded templates of Wallace et al., Gene 16:21-26 (1981).

B. Methods for the Isolation of Nucleic Acids Comprising Isolated BCTV Vaccine Sequences Isolated BCTV vaccine nucleic acids can be isolated using any of a variety of methods known to those of skill in the art which may be used for isolation of nucleic acids. For example, BCTV vaccine sequences are prepared from isolated BCTV nucleic acids. BCTV nucleic acids can be isolated from purified from curtovirus-infected plant tissue using any of several available total nucleic acid purification methods commonly known to those with skill in the art (see e.g., Dellaprta, S., Wood, J., and Hicks, J. B. 1983. A plant DNA minipreparation: Version II. Plant Molecular Biology Reporter 1: 19-21.1983).

In one exemplary embodiment BCTV nucleic acids used for the preparation of isolated BCTV vaccine sequences are isolated from plant tissue infected with Beet severe curly top virus (BSCTV; GenBank Accession Number NC_004754). In another exemplary embodiments BCTV nucleic acids used for the preparation of isolated BCTV vaccine sequences are isolated from plant tissue infected with Beet mild curly top virus (BMCTV; NC_004753). In still another exemplary embodiment BCTV nucleic acids are used for the preparation of isolated BCTV vaccine sequences are isolated from plant tissue infected with Beet curly top virus (BCTV; NC_001412).

In another exemplary embodiment, the nucleic acid sequences comprising isolated BCTV nucleic acid sequences and related nucleic acid sequences are cloned from genomic DNA libraries using amplification techniques and labeled oligonucleotide primers.

Isolated BCTV vaccine sequences typically comprise sequences that are identical to, or show substantial sequence identity (as defined above) to SEQ ID NO:10 (Construct #1 sense) and consist of a nucleotide sequence according to SEQ ID NO:14 (Construct #2), SEQ ID NO:17 (construct #3) or segment or fragment thereof. Thus, in exemplary embodiments, an isolated BCTV vaccine sequence is a member selected from the group consisting of SEQ ID NO:10, SEQ ID NO:14, and SEQ ID NO:17, variants thereof, and fragments thereof. In another exemplary embodiment, variants of isolated BCTV vaccine nucleic acids have at least about 80% sequence identity, at least about 85% sequence identity or at least about 90%, 90%, 91%, 92%, 93%, 94%, 95%, 96%, 97%, 98%, 99%, or 100%, sequence identity to SEQ ID NO:10, SEQ ID NO:14, or SEQ ID NO:17 and thus consist essentially of a nucleotide sequence according to SEQ ID NO:10, SEQ ID NO:14, or SEQ ID NO:17 or segments or fragments thereof.

Thus, isolated BCTV nucleic acid sequences typically hybridize to SEQ ID NO:10, SEQ ID NO:14 or SEQ ID NO:17 under stringent hybridization conditions.

Other methods known to those of skill in the art can also be used to isolate DNA fragments comprising isolated BCTV nucleic acids for the preparation of BCTV vaccine sequences. See e.g., Sambrook, et al. for a description of other techniques for the isolation of DNAs related to DNA molecules of known sequence and the construction of artificial DNA sequences.

Once a putative isolated BCTV vaccine sequence is prepared from isolated BCTV nucleic acid sequences, it can be tested for virus control activity, e.g, tested for the ability to confer immunity to BCTV. Methods for testing the activity of BCTV in plant cells are known in the art (see e.g., Wintermantel, W. M. and Kaffka, S. R. 2006. Plant Disease 90: 657-662; Chen et al., 2010; Chen, L. F., Vivoda, E., and Gilbertson, R. L. 2010. Arch Virol. 2011 156(4): 547-555; Strausbaugh, C. A., Wintermantel, W. M., Gillen, A. M., and Eujayl, I. A. 2008. Curly top survey in the western United States. Phytopathology 98: 1212-1217.)

Briefly, susceptible plants are inoculated with vaccines protective against BCTV and related curtoviruses as disclosed herein. To determine if vaccination was successful and has therefore conferred immunity/resistance to BCTV, PCR with BCTV-specific primers is conducted by methods known in the art (see e.g., Strausbaugh et al., (2008) supra). Thus, immunity is indicated by a lack of development of disease symptoms and confirmation of lack of infection by an inability to detect virus nucleic acid using PCR based detection, or the inability to detect virus protein using serological testing methods such as ELISA, when control (untreated) plants develop infection at a high rate (85% or higher).

Thus, isolated BCTV vaccine sequences that hybridize to SEQ ID NO:10, SEQ ID NO:14, or SEQ ID NO:17 under stringent hybridization conditions are tested for their ability to confer immunity to BCTV and related curtoviruses in susceptible plants e.g., beets, tomatoes, by methods known in the art.

Sequence Features of Isolated BCTV Vaccine Sequences

The full length isolated The Beet severe curly top virus (BSCTV) genome is known in the art and is available as Accession No. NC_004754 from the National Center for Biotechnology Information, NIH, Bethesda, Md. 20894, USA. See also Drake C. Stenger, (1994) Mol. Plant Microbe Interact. 7 (1), 154-157. The genomes of other curtoviruses capable of inducing curly top disease exhibit similar genomic organization (e.g. Stanley et al., 1986: EMBO J. 5: 1761-1767).

FIG. 1 illustrates the genomic organization of Beet severe curly top virus (BSCTV) and is generally representative of the genomes of other curtoviruses, including BMCTV, BCTV, and others.

Features that contribute to an effective curtovirus (e.g., BCTV) vaccine include the design of BCTV nucleic acid sequences into structures and arrangements that facilitate gene silencing. This includes sequences having a relatively high level of identity (89% or greater) with the target viruses, which includes BSCTV, BMCTV, BCTV, and other members of the genus, Curtovirus. Silencing constructs were designed to share at least about 89% identity/similarity with BSCTV, BMCTV, BCTV. In exemplary embodiments, BCTV nucleic acid sequences are cloned from the genomes of BMCTV and BSCTV, however, sequences cloned from other curtoviruses may also share such levels of identity in these select regions of the viral genome as well and thus, would have the same effect. Regions included for control include nucleic acids encompassing the C1/C4 protein encoding region, clockwise through the origin of replication (FIG. 1).

Changes to the sequence that reduce genomic similarity to below 89% compared to these genomes might prevent effectiveness against these viruses.

Figure 2:
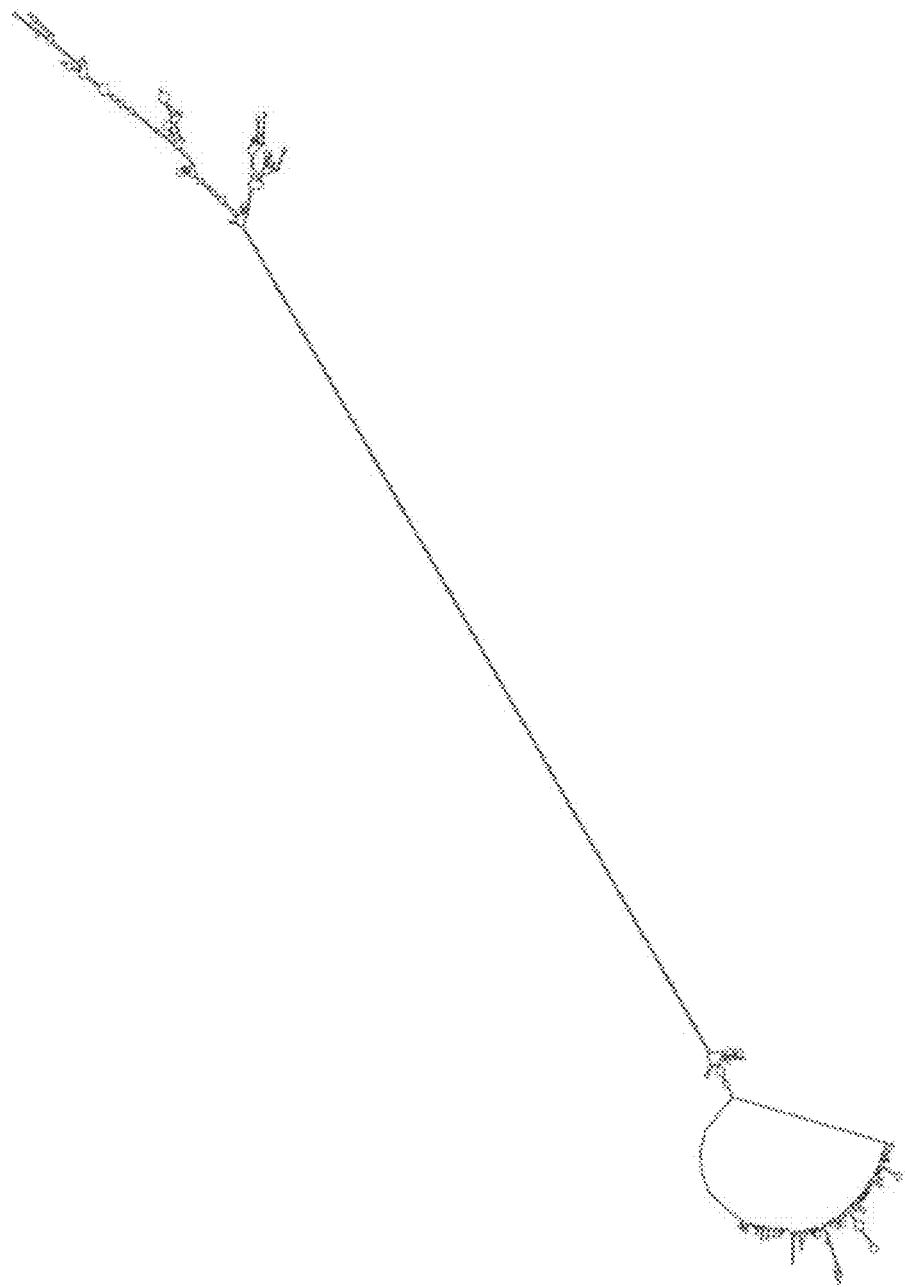
FIG. 2 MFold analysis of hairpin shaped small folded RNA produced by pFGC5941-CurtovirusHP (Mfold web server for nucleic acid folding and hybridization prediction Nucl. Acids Res. (2003) 31(13): 3406-3415).
Figure 3:
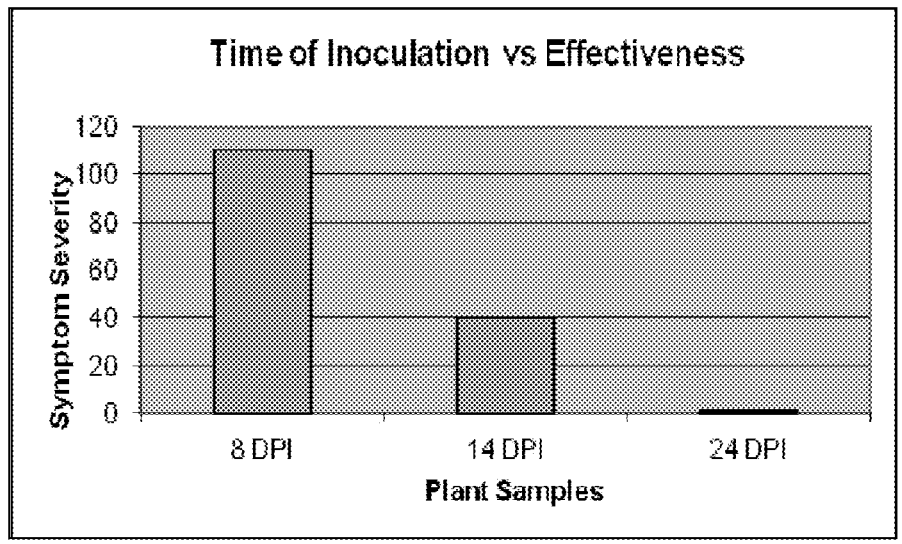
FIG. 3 Comparison of curly top symptom severity when plants were inoculated at 8, 14 and 24 days post-treatment with silencing construct pFGC5941-curtovirusHP, illustrating near complete control of BSCTV when inoculated with BSCTV 24 days after treatment.
Figure 4:
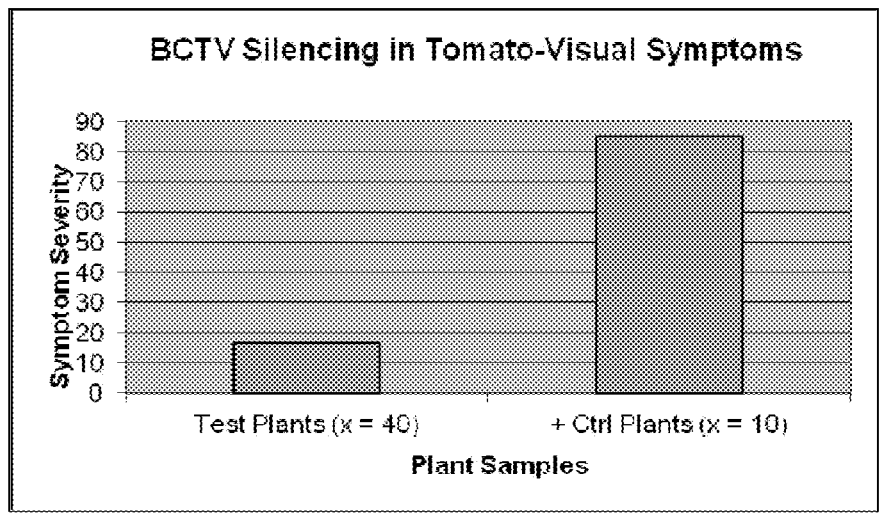
FIG. 4 Effectiveness of pFGC5941-curtovirusHP treatment for control of Beet severe curly top virus when inoculated with virus at 20 days following treatment using agroinoculation with BSCTV. Results represent composite of two separate replications of 20 treated plants each.

In addition to sequence similarity, which is a primary determinant for effectiveness of silencing with vaccine constructs 2 and 3, the design of the hairpin structure used in vaccine construct #1 is also relevant. In vaccine construct #1, three segments of the BSCTV genome, including regions encoding adjacent ends of proteins C1 and C2, C2 and C3, and V1 and V2 (FIG. 1) were assembled sequentially to form a linear (+) sense sequence, followed by an intron, then the inverted (−) sense sequence, allowing formation of a hairpin structure in vivo (FIG. 2). This functional, synthetic structure is responsible for induction of gene silencing. Alteration of any of the three segments in either DNA strand (sense or antisense), to render identity to BSCTV, BMCTV or BCTV lower than 89% could potentially interfere with gene silencing. However, rearrangement of any of these sequences would likely still result in the silencing effect due to the nature of gene silencing and the role of small RNAs (see e.g., Voinnet O (2001) *Trends Genet,* 17, 449-459).

C. Construction of Vectors Comprising Isolated BCTV Vaccine Sequences

Once an isolated BCTV vaccine sequence been prepared/isolated, various methods may be used to construct expression cassettes, vectors and other DNA constructs. Expression cassettes comprising isolated BCTV vaccine sequence can be constructed in a variety of ways. The skilled artisan is well aware of the genetic elements that must be present on an expression construct/vector in order to successfully transform, select and propagate the expression construct in host cells. Techniques for manipulation of nucleic acids encoding isolated BCTV vaccine sequences such as subcloning nucleic acid sequences into expression vectors, labeling probes, DNA hybridization, and the like are described generally in Sambrook, et al., supra.

In an exemplary embodiment, an isolated BCTV vaccine sequence is cloned into an expression vector via suitable restriction endonuclease sites such that a promoter is upstream of and in-frame with the BCTV vaccine sequence.

DNA constructs comprising an isolated BCTV vaccine nucleic acid operably linked to a promoter sequence can be inserted into a variety of vectors (e.g., pFGC5941 available as accession number Vector: 1004952070 from The *Arabidopsis* Information Resource (TAIR) located at the Carnegie Institution for Science Department of Plant Biology, Stanford, Calif.). Typically, the vector chosen is an expression vector that is useful in the transformation of plants and/or plant cells. The expression vector may be a plasmid, virus, cosmid, artificial chromosome, nucleic acid fragment, or the like. Such vectors can be constructed by the use of recombinant DNA techniques well known to those of skill in the art. The expression vector comprising an isolated BCTV vaccine sequence may then be transfected either stably or transiently into the susceptible host plants. Successfully transfected plants are identified based the development of immunity to BCTV infection.

A number of recombinant vectors are available to those of skill in the art for use in the stable transfection of plant cells or for the establishment of transgenic plants (see e.g., Weissbach and Weissbach, (1989) *Methods for Plant Molecular Biology,* Academic Press; Gelvin et al., (1990) *Plant Molecular Biology Manual; Genetic Engineering of Plants, an Agricultural Perspective,* A. Cashmore, Ed.; Plenum: NY, 1983; pp 29 38; Coruzzi, G. et al., The Journal of Biological Chemistry, 258:1399 (1983); and Dunsmuir, P. et al., Journal of Molecular and Applied Genetics, 2:285 (1983). As is known in the art, the choice of a vector is influenced by the method that will be used to transform host plants, and appropriate vectors are readily chosen by one of skill in the art. In an exemplary embodiment, known vectors are used to create expression constructs comprising isolated BCTV vaccine sequences.

D. Plant Hosts, Plant Transformation and Plant Selection and Regeneration Techniques DNA constructs comprising an isolated BCTV vaccine sequence operably linked to a heterologous promoter sequence can be used to transfect plant cells and produce plants with desired phenotypic characteristics e.g., immunity to BCTV.

Exemplary plants for transformation with expression constructs comprising isolated BCTV vaccine sequences include, but are not limited to; to sugar beet (*Beta vulgaris*), bean (*Phaseolus vulgaris*), pepper (*Capsicum* ssp), tomato (*Solanum lycopersicum*), potato (*Solanum tuberosum*), members of the genus *Cucurbita* e.g., Hubbard squash (*C. Hubbard*), Butternut squash (*C. moschtata*), Zucchini (*C. pepo*), members of the genus *Cucumis* such as cucumber (*Cucumis sativus*), cantaloupe (*C. cantalupensis*), and musk melon (*C. melo*). Ornamental plants e.g., azalea (*Rhododendron* spp.), hydrangea (*Macrophylla hydrangea*), arabidopsis (*Arabidopsis thaliana*), etc.

Transformation and regeneration of dicotyledonous plant cells is well known in the art, see e.g., Weising et al. Ann. Rev. Genet. 22:421-477 (1988); U.S. Pat. No. 5,679,558; *Agrobacterium Protocols* Kevan M. A. Gartland ed. (1995) Humana Press Inc. and Wang, M., et al. (1998) Acta Hort. (ISHS) 461:401-408. The choice of method varies with the type of plant to be transformed, the particular application and/or the desired result. The appropriate transformation technique is readily chosen by the skilled practitioner.

Exemplary transformation/transfection methods available to those skilled in the art include, but are not limited to: direct uptake of foreign DNA constructs (see e.g., EP 295959); techniques of electroporation (see e.g., Fromm et al., (1986) Nature (London) 319:791) high-velocity ballistic bombardment with metal particles coated with the nucleic acid constructs (see e.g., Kline et al., Nature (London) 327:70 (1987), and U.S. Pat. No. 4,945,050); methods to transform foreign genes into commercially important crops, such as rapeseed (see De Block et al., Plant Physiol. 91:694 701 (1989)), sunflower (Everett et al., Bio/Technology 5:1201 (1987)), soybean (McCabe et al., Bio/Technology 6:923 (1988); Hinchee et al., Bio/Technology 6:915 (1988); Chee et al., Plant Physiol. 91:1212 1218 (1989); Christou et al., Proc. Natl. Acad. Sci USA 86:7500 7504 (1989); EP 301749), rice (Hiei et al., Plant J. 6:271 282 (1994)), corn (Gordon-Kamm et al., Plant Cell 2:603 618 (1990); Fromm et al., Biotechnology 8:833 839 (1990)), and Hevea (Yeang, H. Y., et al., In, Engineering Crop Plants for Industrial End Uses. Shewry, P. R., Napier, J. A., David, P. J., Eds.; Portland: London, 1998; pp 55 64). Other known methods are disclosed in e.g., U.S. Pat. Nos. 5,597,945; 5,589,615; 5,750,871; 5,268,526; 5,262,316; and 5,569,831.

Another exemplary method includes: transformation with DNA employing *Agrobacterium tumefaciens* or *Agrobacterium rhizogenes* as the transforming agent, electroporation, particle acceleration, etc. (see, e.g., EP 295959 and EP 138341). In one exemplary embodiment, Ti-derived vectors are used to transform a wide variety of higher plants, including dicotyledonous plants, such as e.g., potato, soybean, cotton, rape, tobacco, and rice (see e.g., Pacciofti et al., Bio/Technology 3:241 (1985); Byme et al., Plant Cell, Tissue and Organ Culture 8:3 (1987); Sukhapinda et al., Plant Mol. Biol. 8:209 216 (1987); Lorz et al., Mol. Gen. Genet. 199:178 (1985); Potrykus, (1985) supra; Park et al., J. Plant Biol. 38(4):365 71 (1995); and Hiei et al., Plant J. 6:271 282 (1994)).

*Agrobacterium tumefaciens*-meditated transformation techniques are well described in the scientific literature. See, e.g., Horsch et al. Science (1984) 233:496-498, and Fraley et al. (1983) Proc. Natl. Acad. Sci. USA 80:4803. Typically, a plant cell, an explant, a meristem or a seed is infected with *Agrobacterium tumefaciens* transformed with the expression vector/construct which comprises an isolated BCTV vaccine sequence. Under appropriate conditions known in the art, the transformed plant cells are grown to form shoots, roots, and develop further into plants. The nucleic acid segments can be introduced into appropriate plant cells, for example, by means of the Ti plasmid of *Agrobacterium tumefaciens*. The Ti plasmid is transmitted to plant cells upon infection by *Agrobacterium tumefaciens*, and is stably integrated into the plant genome (Horsch et al., (1984) "Inheritance of Functional Foreign Genes in Plants," Science, 233:496-498; Fraley et al., (1983) Proc. Nat'l. Acad. Sci. U.S.A. 80:4803.

Plants and plant cells can be transfected/transformed either stably or transiently. Plant cells stably transformed by *Agrobacterium* and whole plants regenerated from the transformed cells can also be transformed so as to produce transformed whole plants which contain the transferred expression vector/construct which comprises an isolated BCTV vaccine sequence.

Transformed plant cells which are stably constructed by any of the above transformation techniques can be cultured to regenerate a whole plant which possesses the desired transformed phenotype. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans et al., Protoplasts Isolation and Culture, Handbook of Plant Cell Culture, pp. 124-176, MacMillan Publishing Company, New York, 1983; and Binding, Regeneration of Plants, Plant Protoplasts, pp. 21-73, CRC Press, Boca Raton, 1985, all of which are incorporated herein by reference. Regeneration can also be obtained from plant callus, explants, organs, or parts thereof. Such regeneration techniques are described generally in Klee et al. Ann. Rev. of Plant Phys. 38:467-486 (1987).

One of skill will recognize that, after an expression cassette comprising isolated BCTV nucleic acid sequences is stably incorporated in transgenic plants and confirmed to be operable, it can be introduced into other plants by sexual crossing. Any of a number of standard breeding techniques can be used, depending upon the species to be crossed.

In some exemplary embodiments, susceptible plant hosts are transiently transfected with an expression vector/construct which comprises an isolated BCTV vaccine sequence.

In one exemplary embodiment, an expression vector/construct comprising an isolated BCTV vaccine sequence is transfected into a susceptible host plant by direct injection (see e.g., Plant Journal, Ryu et al., 2004, which is incorporated herein by reference). In one exemplary embodiment, an expression vector/construct comprising an isolated BCTV vaccine sequence is transfected into a susceptible host plant by Airbrush spray method (see e.g., Dinesh-Kumar, Cold Spring Harbor protocol 2009, which is incorporated herein by reference).

The following examples are offered to illustrate, but not to limit the invention.

EXAMPLES

Example 1

The following Example illustrates preparation of DNA constructs comprising BCTV vaccine nucleic acids.
Constructs for Induction of Gene Silencing
Vaccine Construct #1: pFGC5941-CurtovirusHP This construct, pFGC5941-CurtovirusHP, produces a hairpin configuration of nucleic acid, an RNA structure known to induce gene silencing against many types of RNAs. The hairpin in pFGC5491-BSCTV comprises three separate regions of the Beet severe curly top virus (BSCTV) genome (see arrows indicating genomic locations in BSCTV diagram FIG. 1) combined to form a hairpin-shaped construct. The construct was designed by combining portions of these three genomic regions adjacent to one another in two constructs as disclosed hereinbelow. SEQ ID NO:10 is in the sense or coding orientation, whereas SEQ ID NO:11 is a complementary sequence in the antisense orientation. pFGC5941-CurtovirusHP was constructed based on methods known in the art for a distantly related member of the Geminiviridae (see e.g., Abhary et al., 2006 Arch. Virol. 151: 2349-2363).

Briefly, three regions of the BSCTV genome (312 nt of the C1/C2 coding region, 250 nucleotides (nt) of the C2/C3 coding region, and 212 nt of V1/V2 coding region) were amplified by PCR and cloned separately in both sense and antisense directions into the binary vector, pFGC5941. pFGC5941 contains a CHSA (Chalcone Synthase A) intron, resulting in production of a hairpin structure once both sense and antisense regions are incorporated on either side of the CHSA intron. pFGC5941 is available as accession number Vector: 1004952070 from The *Arabidopsis* Information Resource (TAR) located at the Carnegie Institution for Science Department of Plant Biology, Stanford, Calif. A diagram of the construct as folded nucleic acid is shown in FIG. 2.

Vaccine construct 1 was prepared by first cloning the individual sequences of the three above named genomic regions individually into the TOPO® TA vector (Life Technologies). The sequence of each region is shown below.

C1/C2 SUBCLONE: Primers 1863F (SEQ ID NO:1): ATATGGATCCATTTAAAT TTACAYGGYAGWTTGARCTTGC and 2174R (SEQ ID NO:2): ATATAAGCTTGTTYTRTATAACGTCATTGAT-GAC were used in PCR to amplify and clone a portion of the genes encoding the C1/C2 proteins of BCTV Restriction sites for cloning BamH1 and SwaI are shown in bold and italicized font, respectively on 1863F primer. HINDIII is shown in bold, italicized font on 2174R primer. The complete sequence of the resulting C1/C2 subclone is shown below (SEQ ID NO:3):

```
ATATGGATCCATTTAAATTTACATGGCAGATTGAGCTTGCGAGGACGCTT

CTTGATTGTTATCAAAGAGAGGACTTGTGAGTTTGGCGAAGACTGAATTT

TGTAATGTCCAGGACCTAAGGGCTTCATTTTCTGATTTATTGAGGAAGTC

CTGGTAAGAGCTGCCTTCGCCTGGATTGCATAATATAATACTGGGAATAC

CACCTTTAATGACACGTGGTTTTCCATACTTTAAGTTTGTCTGCCACTCT

CTTTGTGCGCCTATAAGGTGCTTCCAATGCTTCATCTTTAAGTAATTTGG

ATCTACGTCATCAATGACGTTATATAGAACAAGCCCTATAT
```

C2/C3 SUBCLONE: Primers 1584F ATATCTCGAGC-TYTCAAAAAACGGTCYCCAG (SEQ ID NO:4): and 1832R (SEQ ID NO:5): TTAAAAGCTTA TCASGGATTTTCGCACRGAR were used to clone portions of the genes encoding the C2/C3 proteins of BSCTV. Primer 1584F sequence (underlined) begins at nt 1584 with a four nt generic leader, followed by a XhoI site (bold italic) ahead of BCTV primer sequence. Primer 1832R contains a four nt generic leader followed by an HindIII site and BCTV sequence. The complete sequence of the resulting C2/C3 subclone is shown below (SEQ ID NO:6):

```
ATATCTCGAGCTTTCAAAAAACGGTCCCCAGTTAATGTCCTGTGTGCTCC
```

```
AGTGATCGTCAAATCTATCCAGCACTTGTGAAGATTCAAGTATTTGCGGA

GGTTGTGGTTGAATCTTATCTGGACTTTCAGTTGATAAACTGGCCCGGAA

CGGAAGAAGTCCTGGAGTTTGAGGTACAATGGATTGGGTACCAAGTCCAC

GGGTATGGAATTCGTCGCTTGTTGCAGCGTGATGGGTTCCTCCGTGCGAA

AATCCCTGAAAAGCTTTTAA
```

V1/V2 Subclone:

Primers 700F and 911R were used to clone a portion of the genes encoding the V1/V2 proteins of BSCTV. Primer sequence matching BSCTV sequence is underlined. Primer 700F (SEQ ID NO:7): TCATTCTAGAGGCGCGCC TGAATCCTCAAAGTGCGTGGC contains XbaI and AscI restriction sites and a four nt generic leader, and primer 911R (SEQ ID NO: 8): ATTTCTCGAG TCTCTGACTATCACCAATACCCTGG contains an XhoI site and a four nt generic leader.

The complete sequence of the resulting V1/V2 subclone is shown below (SEQ ID NO:9):

```
TCATTCTAGAGGCGCGCCTGAATCCTAAAGTGCGTGGCCGAAGAAGAGGA

GGACTACTACGATTTCGAGGAAATACCAATGGAGGAGACCTGTGACAAAA

AACAGGACTCTGAAGTTAAAGATGTATGATGATATGTTGGGTGCTGGTGG

TATAGGATCTACCATTAGTAATAATGGTATGATTACTATGTTGAATAATT

ATGTCCAGGGTATTGGTGATAGTCAGAGACTCGAGAAAT
```

C1/C2 and C2/C3 subclone sequences were assembled using restriction enzyme sites designed into primers shown above into the TOPO® TA plasmid vector to form Subclone C1/C2/C3. The insert in Subclone C1/C2/C3 was subsequently excised and ligated back into Subclone V1/V2 in the TOPO® TA vector between the BamHI and XhoI sites, ahead of the V1/V2 insert to form the combined construct, Subclone C1/C2/C3/V1/V2. The complete insert in Subclone C1/C2/C3/V1/V2 was excised using XbaI and BamHI enzymes, and ligated in sense orientation into the binary vector, pFGC5941 to create Subclone C1/C2/C3/V1/V2senseHP. The complete insert in Subclone C1/C2/C3/V1/V2 was separately excised using SwaI and AscI and ligated in the antisense orientation into Subclone C1/C2/C3/V1/V2senseHP to create the final construct, pFGC5941BSCTV hairpin. Restriction sites are underlined to assist in the location of segments from each subclone. The final folded structure of the pFGC5941 BSCTV hairpin construct is shown below (FIG. 2).

```
BCTV C1/C2/C3/V1/V2 Sense Direction (in pFGC5941
vector) (SEQ ID NO: 10):
GGCGCGCCTGAATCCTAAAGTGCGTGGCCGAAGAAGAGGAGGACTACTAC

GATTTCGAGGAAATACCAATGGAGGAGACCTGTGACAAAAAACAGGACTC

TGAAGTTAAAGATGTATGATGATATGTTGGGTGCTGGTGGTATAGGATCT

ACCATTAGTAATAATGGTATGATTACTATGTTGAATAATTATGTCCAGGG

TATTGGTGATAGTCAGAGACTCGAGCTTTCAAAAAACGGTCCCCAGTTAA

TGTCCTGTGTGCTCCAGTGATCGTCAAATCTATCCAGCACTTGTGAAGAT

TCAAGTATTTGCGGAGGTTGTGGTTGAATCTTATCTGGACTTTCAGTTGA

TAAACTGGCCCGGAACGGAAGAAGTCCTGGAGTTTGAGGTACAATGGATT

GGGTACCAAGTCCACGGGTATGGAATTCGCCCTTATATAGGGCTTGTTCT

ATATAACGTCATTGATGACGTAGATCCAAATTACTTAAAGATGAAGCATT

GGAAGCACCTTATAGGCGCACAAAGAGAGTGGCAGACAAACTTAAAGTAT

GGAAAACCACGTGTCATTAAAGGTGGTATTCCCAGTATTATATTATGCAA

TCCAGGCGAAGGCAGCTCTTACCAGGACTTCCTCAATAAATCAGAAAATG

AAGCCCTTAGGTCCTGGACATTACAAAATTCAGTCTTCGCCAAACTCACA

AGTCCTCTCTTTGATAACAATCAAGAAGCGTCCTCGCAGCTCAATCTGCC

ATGTAAATTTAAAT

BCTV C1/C2/C3/V1/V2 Antisense Direction (in
pFGC5941 vector) (SEQ ID NO: 11):
GATCCATTTAAATTTACATGGCAGATTGAGCTTGCGAGGACGCTTCTTGA

TTGTTATCAAAGAGAGGACTTGTGAGTTTGGCGAAGACTGAATTTTGTAA

TGTCCAGGACCTAAGGGCTTCATTTTCTGATTTATTGAGGAAGTCCTGGT

AAGAGCTGCCTTCGCCTGGATTGCATAATATAATACTGGGAATACCACCT

TTAATGACACGTGGTTTTCCATACTTTAAGTTTGTCTGCCACTCTCTTTG

TGCGCCTATAAGGTGCTTCCAATGCTTCATCTTTAAGTAATTTGGATCTA

CGTCATCAATGACGTTATATAGAACAAGCCCTATATAAGGGCGAATTCCA

TACCCGTGGACTTGGTACCCAATCCATTGTACCTCAAACTCCAGGACTTC

TTCCGTTCCGGGCCAGTTTATCAACTGAAAGTCCAGATAAGATTCAACCA

CAACCTCCGCAAATACTTGAATCTTCACAAGTGCTGGATAGATTTGACGA

TCACTGGAGCACACAGGACATTAACTGGGGACCGTTTTTTGAAAGCTCGA

GTCTCTGACTATCACCAATACCCTGGACATAATTATTCAACATAGTAATC

ATACCATTATTACTAATGGTAGATCCTATACCACCAGCACCCAACATATC

ATCATACATCTTTAACTTCAGAGTCCTGTTTTTTGTCACAGGTCTCCTCC

ATTGGTATTTCCTCGAAATCGTAGTAGTCCTCCTCTTCTTCGGCCACGCA

CTTTAGGATTCAGGCGCGCC
```

Vaccine Construct #2:

Briefly, pTRV-CFH1 involved cloning a region of BSCTV into a virus-based gene expression vector comprising of a modified Tobacco rattle virus RNA2 (pTRV2) clone inserted into an *Agrobacterium* vector (see e.g., Dinesh-Kumar et al., Plant J. (2002) September; 31(6):777-86). A 415 nt section of the region encoding the C4 protein within the Rep gene (C1), corresponding to nt 2538-nt 25, and encompassing the origin of replication of BSCTV was amplified by PCR and inserted into the multiple cloning site (MCS) between BamHI & EcoRI in the pTRV2 vector (see e.g., Dinesh-Kumar et al., 2002, supra) which uses a double 35S promoter to induce Virus Induced Gene Silencing (VIGS), to form pTRV-CFH1. pTRV-CFH1 requires addition of pTRV1, which encodes the TRV RNA1 (pTRV1) genome necessary for function in planta. pTRV1 is also expressed in an *Agrobacterium* vector (see e.g., Dinesh-Kumar et al., Plant J. (2002) September; 31(6):777-86). Both pTRV1 and pTRV-CFH1 are agroinoculated together to deliver the TRV to the plant, carrying the silencing inducer construct.

Primers used to amplify BSCTV insert for vaccine construct #2: Primer 2538F GCATATGGATCC TGCAGCATCATTAGCCGTCTG, (SEQ ID NO:12) which includes a six nt leader sequence and a BamHI restriction site. Primer 25R CCGAATCC GGATTTGAAGAGAGCCCGATTC, (SEQ ID NO:13) which includes a 2 nt leader sequence and an EcoRI restriction site.

Sequence of Vaccine Construct 2 silencing construct encompassing nt 2538-nt 25 of genome of BSCTV (NC_004754).

(SEQ ID NO: 14)
TGCAGCATCATTAGCCGTCTGTTGACCTCCGCGTGCAGATCTTCCATCGA

CCTGAAATTCACCCCAGTCGATGTGATCTCCGTCCTTTGAGACGTAGGAC

TTGACGTCGGAACTGGATTTAGCTCCCTGAATATTGCAGTGGAATTGTTT

GCTGGTACTTCGATGTTGCAGATCGAAGTAACGGGCATTACGGATCTGGA

CTTTTCCTTCGAATTGAATAAGGGCATGCAGATGTGGTTCCCCATTTTCA

TGTAATTCTCTGCAGATGCGAATATATTTTTTATTCGAAGGTGTATTTAT

AGCGAGGAGCTGTTCTAAGGCGTCTTCTTTGGTTACTGAACATTGAGGGT

ATGTAAGGAAAAAATTTTTGGCTTTTTTGTAAAAAGGCATATTGAATCGG

GCTCTCTTCAAATCC

Vaccine Construct #3:

pTRV-CFH/WOR. This construct was designed from the 3' terminal 312 nt of the C1 region, which encodes the curtovirus replication protein. Assembly involved PCR amplification of the region from nt 1863-2174 near the 3' end of the C1 gene of BSCTV (NC_004754) and the corresponding sequence with Beet mild curly top virus (BMCTV; Accession No. NC_004753) and cloning into the NcoI & BamHI sites of pTRV2 (see e.g., Dinesh-Kumar et al., 2002, supra) using PCR amplification of the viral genomic segment and primers including restriction enzyme sites utilized for cloning into pTRV2. Primer sequences are Primer VC3_1863F GATCGGA TTCTTACAYGGYAGWTTGARCTTGC (SEQ ID NO: 15), which includes a 4 nt leader sequence and a BamHI restriction site, and Primer VC_2173R GATCCCATGGGT-TYTRTATAACGTCATTGATGAC (SEQ ID NO: 16), which includes a 4 nt leader sequence and an NcoI restriction site.

Vaccine Construct #3: Sequence of BSCTV sequence Vaccine Construct in pTRV-CFH/WOR, encompassing nucleotides 1863-2174 BSCTV, but also corresponding to same region of BMCTV and related to other viruses within the genus. pTRV-CFH/WOR (SEQ ID NO:17):

TTACAAGGAAGTTTGATCTTGCGAGGACGCTTCTTGATTGTTATCAAAGA

GAGGACTTGTGAGTTTGGCGAAGACTGAATTTTGTAATGTCCAGGACCTA

AGGGCTTCATTTTCTGATTTATTGAGGAAGTCCTGGTAAGAGCTGCCTTC

GCCTGGATTGCATAATATAATACTGGGAATACCACCTTTAATGACACGTG

GTTTTCCATACTTTAAGTTTGTCTGCCACTCTCTTTGTGCGCCTATAAGG

TGCTTCCAATGCTTCATCTTTAAGTAATTGGGATCTAC<u>GTCATCAATGAC</u>

<u>GTTATACAGAAC</u>

All three constructs for induction of gene silencing were transformed into *Agrobacterium tumefaciens* strain AGL1 for delivery to plants. *Agrobacterium tumefaciens* strain AGL1 is known in the art (see e.g., Lazo G R, et al (1991) Biotechnology (NY) October; 9(10):963-967).

Example 2

The following Example illustrates delivery of gene silencing inducer constructs using *A. tumefaciens* strain AGL1 and various delivery systems into *Nicotiana benthamiana*, and tomato, *Solanum lycopersicum*, with the DNA construct disclosed in Example 1. Delivery method #1: Direct injection into plants is known in the art (see e.g., Ryu et al., (2004) The Plant Journal 40:322-331). Vaccines 2 and 3 (See Example 1) were delivered using the TRV vector and consisted of TRV RNA1 and the gene silencing inducer construct inserted into a TRV RNA2 vector (Dinesh-Kumar, et al, 2002, supra) mixed in a 1:1 ratio. pTRV1 and either pTRV-CFH1 (vaccine construct 2) or pTRV-CFH/WOR (vaccine construct 3), described above, which are inserted into pTRV2, the cloned version of TRV RNA2. The *Agrobacterium* carrying each construct in TRV was grown separately to log phase at 30° C., chilled, centrifuged at low speed, and the cells were resuspended in a buffer consisting of 10 mM MES, 10 mM $MgCl_2$ and 400 uM acetosyringone to an absorbance of 1.0 at OD600, after which the cells were grown an additional 4 hours at 30° C. Approximately 100 μL was injected directly into the stem of each of the test plants or infiltrated into two leaves using a needleless syringe.

Constructs were also delivered to plants via Delivery method #2: Airbrush. Airbrush is known in the art (see e.g., Dinesh-Kumar, Cold Spring Harbor protocol 2009). The *Agrobacterium* carrying each construct was grown separately was grown to log phase at 30° C., chilled, centrifuged at low speed, and the cells were resuspended in a buffer consisting of 10 mM MES, 10 mM $MgCl_2$ and 400 uM acetosyringone to an absorbance of 1.5-2.0 at OD600, after which the cells were grown an additional 4 hours at 30° C. Loaded agrobacterium suspension into an artist's airbrush (Paasche VL) and sprayed the ventral side of test plants at 80 psi from approximately 8 inches distance for about 3-5 seconds. Approximately 1 mL solution was used per plant.

No carriers were used for delivery of constructs other than the MES/$MgCl_2$/Acetosyringone buffer solution described above.

Lifetime of immunity was not conclusively determined due to laboratory testing limitations, but was effective until age related resistance develops as seedlings mature. Virus inoculations were conducted at up to 45 days post treatment to determine if resistance remained effective however, plants at that age are so large that the positive controls no longer develop disease symptoms, and virus may or may not accumulate significantly in such plants (referred to as age-related resistance). Essentially the treatment method is protecting the young plants during their most susceptible period. Once plants obtain substantial size and age, they seem to develop age related resistance, or at least require higher levels of innoculum than was possible in the lab to develop infection.

Maximum gene silencing based suppression of virus occurs after 18-20 days post inoculation, based on levels of virus detected by qPCR. Plants were assayed for evaluation of resistance following treatment either with injection or spray, by inoculation with curtoviruses BSCTV and/or BMCTV, visually scoring plants for symptom development at 3 weeks post-inoculation, and extracting total nucleic acid from non-inoculated leaves and testing by PCR using standard primer sequences for detection of BSCTV and BMCTV as described in Strausbaugh, C. A., Wintermantel, W. M., Gillen, A. M., and Eujayl, I. A. 2008. Curly top survey in the western United States. Phytopathology 98: 1212-1217.

Example 3

The following Example illustrates results of an exemplary method for detection of immunity to BCTV infection by induced gene silencing.

Testing of plants for infection by BSCTV and BMCTV was performed using both natural transmission of virus by beet leafhopper (*C. tenellus*) (see e.g., Wintermantel, W. M. and Kaffka, S. R. 2006. Plant Disease 90: 657-662) and using *Agrobacterium tumefaciens* to deliver virus to the plant (see e.g., Chen, L. F., Vivoda, E., and Gilbertson, R. L. 2010. Arch Virol. 2011 156(4): 547-555). All experiments were performed in growth chambers under standard conditions, 16 hour days, 25° C. Confirmation of infection of test plants was performed using PCR with BSCTV and BMCTV-specific primers by methods known in the art (see e.g., Strausbaugh, C. A., et al (2008) supra).

TABLE 1

Results of testing resistance against curtoviruses using virus induced gene silencing.
Curly Top Virus Silencing in Tomato and Benth

| Construct | Tomato | Benth |
| --- | --- | --- |
| TRV-CFH1 (Trial 1)[1] | 13/14 | 3/3 |
| TRV-CFH1 (Trial 2)[1] | 15/15 | NA |
| Agrovector-BCTV Hairpin (Trial 1)[1] | 6/6 | 4/6[2] |
| Agrovector-BCTV Hairpin (Trial 2)[1] | 18/20 | NA |
| Agrovector-BCTV Hairpin (Trial 3)[1] | 17/20 (9/20)* | NA |

[1]Testing by ELISA (direct method)
[2]of the 2 that were positive, the abs readings were 2-4X lower than the positive control benth plants
[3]Results of Visual Inspection for BCTV Symptoms
*The positive control plants for Trial 3 were negative by ELISA, therefore the test was rerun.
The retest results are in parantheses where 4/5 positive control plants were positive.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A plant vaccine composition for inducing immunity to Beet Curly Top Virus (BCTV) in a susceptible plant, the plant vaccine comprising: an expression vector comprising a heterologous promoter sequence operably linked to an isolated BCTV vaccine nucleic acid sequence that is selected from the group consisting of (i) SEQ ID NO:14 and (ii) both SEQ ID NO:10 and SEQ ID NO:11.

2. A plant vaccine composition for inducing immunity to Beet Curly Top Virus (BCTV) in a susceptible plant, the plant vaccine comprising: an expression vector comprising a heterologous promoter operably linked to SEQ ID NO:10 wherein SEQ ID NO:10 is operably linked to an intron, and the intron is operably linked to SEQ ID NO:11.

3. The plant vaccine composition of claim 1, wherein the vaccine induces immunity to Beet Curly Top Viruses that are members selected from the group consisting of Beet Severe Curly Top Virus (BSCTV) and Beet Mild Curly Top Virus (BMCTV).

4. The plant vaccine composition of claim 1, wherein the susceptible plant is a member selected from the group consisting of sugar beet (*Beta vulgaris*), tomato (*Solanum lycopersicum*), bean (*Phaseolus vulgaris*), and pepper (*Capsicum* spp.).

5. The plant vaccine composition of claim 4, wherein the susceptible plant is sugar beet.

6. The plant vaccine composition of claim 4, wherein the susceptible plant is tomato.

7. A method for inducing immunity to Beet Curly Top Virus (BCTV) in a susceptible plant, thereby protecting the susceptible plant from infection with BCTV, the method comprising:

(i) transfecting the susceptible plant with a suspension of *Agrobacterium tumefaciens*, wherein the *Agrobacterium tumefaciens* comprises an expression vector comprising a heterologous promoter operably linked to an isolated BCTV vaccine nucleic acid sequence that is selected from the group consisting of (i) SEQ ID NO:14 and (ii) the combination of SEQ ID NO:10 and SEQ ID NO:11, to generate a transformed plant; and (ii) selecting said transformed plant that expresses said isolated BCTV vaccine nucleic acid sequence to produce a vaccinated plant;

wherein expression of the isolated BCTV vaccine nucleic acid sequence in the vaccinated plant induces silencing of the BCTV, thereby protecting the susceptible plant from infection with BCTV.

8. A method for inducing immunity to Beet Curly Top Virus (BCTV) in a susceptible plant, thereby protecting the susceptible plant from infection with BCTV, the method comprising:

(i) transfecting the susceptible plant with a suspension of *Agrobacterium tumefaciens*, wherein the *Agrobacterium tumefaciens* comprises an expression vector comprising a heterologous promoter operably linked to SEQ ID NO:10 wherein SEQ ID NO:10 is operably linked to an intron, and the intron is operably linked to SEQ ID NO:11 to generate a transformed plant, (ii) selecting said transformed plant that expresses said SEQ ID NO:10, intron and SEQ ID NO:11 to produce a vaccinated plant;

wherein expression of the expression vector in the vaccinated plant induces silencing of the BCTV thereby protecting the susceptible plant from infection with BCTV.

9. The method of claim 7, wherein the transfection is transient transfection.

10. The method of claim 9, wherein transient transfection is carried out by direct injection of the suspension of *Agrobacterium tumefaciens* into a stem of the susceptible plant.

11. The method of claim 9, wherein transient transfection comprises spraying the suspension of *Agrobacterium tumefaciens* onto one or more leaves of the susceptible plant.

12. The method of claim 7, wherein the method induces immunity to Beet Curly Top Viruses that are members selected from the group consisting of Beet Severe Curly Top Virus (BSCTV) and Beet Mild Curly Top Virus (BMCTV).

13. The method of claim 7, wherein the susceptible plant is a member selected from the group consisting of sugar beet (*Beta vulgaris*), tomato (*Solanum lycopersicum*), bean (*Phaseolus vulgaris*), and pepper (*Capsicum* spp.).

14. The method of claim 13, wherein the susceptible plant is sugar beet.

15. The method of claim 13, wherein the susceptible plant is tomato.

16. A transformed plant comprising an expression vector wherein said expression vector comprises a heterologous promoter operably linked to a nucleic acid selected from the group consisting of (i) SEQ ID NO:14 and (ii) both SEQ ID NO:10 and SEQ ID NO:11.

17. The transformed plant of claim 16, wherein said plant is selected from the group consisting of sugar beet (*Beta vulgaris*), tomato (*Solanum lycopersicum*), bean (*Phaseolus vulgaris*), and pepper (*Capsicum* spp.).

18. The method of claim 8, wherein the transfection is transient transfection.

19. The method of claim 18, wherein transient transfection is carried out by direct injection of the suspension of *Agrobacterium tumefaciens* into a stem of the susceptible plant.

20. The method of claim 18, wherein transient transfection comprises spraying the suspension of *Agrobacterium tumefaciens* onto one or more leaves of the susceptible plant.

21. The method of claim 18 wherein said transient transfection comprises dipping said susceptible plant into said suspension of *Agrobacterium tumefaciens*.

22. The method of claim 9 wherein said transient transfection comprises dipping said susceptible plant into said suspension of *Agrobacterium tumefaciens*.

23. The plant vaccine composition of claim 1 further comprising a carrier.

24. The plant vaccine composition of claim 23, wherein said carrier comprises 2-(4-morpholine)-ethane sulfonic acid (MES), $MgCl_2$ and acetosyringone.

25. The plant vaccine composition of claim 2 further comprising a carrier.

26. The plant vaccine composition of claim 25, wherein said carrier comprises MES, $MgCl_2$ and acetosyringone.

27. The method of claim 7 wherein said suspension of *Agrobacterium tumefaciens* further comprises MES, $MgCl_2$ and acetosyringone.

28. The method of claim 8 wherein said suspension of *Agrobacterium tumefaciens* further comprises MES, $MgCl_2$ and acetosyringone.

* * * * *